(12) United States Patent
Choi et al.

(10) Patent No.: US 10,339,675 B2
(45) Date of Patent: Jul. 2, 2019

(54) TOMOGRAPHY APPARATUS AND METHOD FOR RECONSTRUCTING TOMOGRAPHY IMAGE THEREOF

(71) Applicant: SAMSUNG ELECTRONICS CO., LTD., Suwon-si (KR)

(72) Inventors: Ki-hwan Choi, Yongin-si (KR); Seok-min Han, Seongnam-si (KR); Sang-wook Yoo, Suwon-si (KR); Jong-hyon Yi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 173 days.

(21) Appl. No.: 15/339,067

(22) Filed: Oct. 31, 2016

(65) Prior Publication Data
US 2017/0206681 A1   Jul. 20, 2017

(30) Foreign Application Priority Data
Jan. 20, 2016   (KR) .................. 10-2016-0007149

(51) Int. Cl.
G06T 11/00 (2006.01)
A61B 6/00 (2006.01)
G06T 7/00 (2017.01)

(52) U.S. Cl.
CPC .......... *G06T 11/003* (2013.01); *A61B 6/5205* (2013.01); *G06T 7/0012* (2013.01);
(Continued)

(58) Field of Classification Search
CPC . A61B 2576/00; A61B 6/5205; G06T 11/003; G06T 2207/10081; G06T 7/0012
See application file for complete search history.

(56) References Cited

U.S. PATENT DOCUMENTS 5,907,594 A    5/1999  Lai
7,602,879 B2   10/2009 Chen et al.
(Continued)

FOREIGN PATENT DOCUMENTS

CN    103356223 A    10/2013
JP    2010-038878 A   2/2010
(Continued)

OTHER PUBLICATIONS

Choi et al., "Super-Resolution CT Imaging via Statistical Learning-based Ray Splitting Approach", Samsung Based Paper Award, 2015, 9 pages total.
(Continued)

*Primary Examiner* — Nirav G Patel
(74) *Attorney, Agent, or Firm* — Sughrue Mion, PLLC

(57) ABSTRACT

A tomography method for generating a computed tomography (CT) image, including generating a first tomography image based on first raw data corresponding to a received X-ray comprising acquired photons; determining second raw data by generating a second tomography image having an increased resolution in comparison with the first tomography image and performing forward projection on the second tomography image; determining third raw data based on a first parameter, the first raw data, and the second raw data; and generating a third tomography image based on the third raw data, wherein the determining of the third raw data may be based on information about a distribution of the acquired photons, the information being included in at least one from among the first raw data and the second raw data.

18 Claims, 14 Drawing Sheets

(52) U.S. Cl.
CPC ......... *G06T 11/005* (2013.01); *A61B 2576/00* (2013.01); *G06T 2207/10081* (2013.01)

(56) References Cited

U.S. PATENT DOCUMENTS

| | | |
|---|---|---|
| 2005/0105693 A1 | 5/2005 | Zhao et al. |
| 2008/0240335 A1* | 10/2008 | Manjeshwar .......... A61B 6/032 378/4 |
| 2012/0213327 A1 | 8/2012 | Boas |
| 2015/0036902 A1 | 2/2015 | Zamyatin et al. |
| 2015/0325010 A1* | 11/2015 | Bedford ................ G06T 11/003 378/19 |

FOREIGN PATENT DOCUMENTS

| | | |
|---|---|---|
| JP | 2010-279576 A | 12/2010 |
| KR | 10-1356881 B1 | 2/2014 |

OTHER PUBLICATIONS

International Search Report (PCT/ISA/210) and Written Opinion (PCT/ISA/237) dated Jan. 10, 2017 issued by the International Searching Authority in counterpart International Application No. PCT/KR2016/010876.

Communication dated Oct. 5, 2018, issued by the European Patent Office in counterpart European Application No. 16886615.0.

Lin Fu et al., "Enhancement of spatial resolution in model-based iterative CT reconstruction by using sinogram preprocessing filters", 2012 IEEE Nuclear Science Symposium and Medical Imaging Conference Record, Oct. 27, 2012, pp. 2278-2281 (4 total pages).

\* cited by examiner

TOMOGRAPHY APPARATUS AND METHOD FOR RECONSTRUCTING TOMOGRAPHY IMAGE THEREOF

CROSS-REFERENCE TO RELATED APPLICATION

This application claims priority from Korean Patent Application No. 10-2016-0007149, filed on Jan. 20, 2016, in the Korean Intellectual Property Office, the disclosure of which is incorporated herein in its entirety by reference.

BACKGROUND

1. Field

The present disclosure relates to tomography apparatuses and methods for reconstructing a tomography image thereof, and more particularly, to tomography apparatuses and methods for reconstructing a tomography image thereof, which may reconstruct a high-resolution tomography image by using the distribution of X-ray information detected by a detector.

2. Description of Related Art

A medical imaging apparatus is an equipment for acquiring an internal structure of an object as an image.

For example, as a non-invasive testing apparatus, a medical image processing apparatus images and processes fluid flows, internal tissues, and structural details inside a body and shows the results thereof to users. A user such as a doctor may diagnose the disease and health condition of a patient by using a medical image output from the medical image processing apparatus.

A tomography apparatus is a typical example of an apparatus for imaging an object by irradiating an X-ray to a patient. Specifically, a computed tomography (CT) apparatus may be an example of the tomography apparatus. As a medical image processing apparatus, a CT apparatus may provide a cross-sectional image of an object. In comparison with a general X-ray apparatus, since the CT apparatus may express an internal structure of an object (e.g., an organ such as a kidney or a lung) in a non-overlapping manner, it is widely used to accurately diagnose a disease. Hereinafter, a medical image acquired by the tomography apparatus will be referred to as a tomography image. Specifically, a medical image acquired by the CT apparatus will be referred to as a CT image.

In order to acquire a tomography image, the tomography apparatus acquires raw data by performing tomography on an object. Then, the tomography apparatus reconstructs a tomography image by using the acquired raw data. Herein, the raw data may include projection data that is acquired by irradiating an X-ray to the object, or a sinogram that is a set of projection data.

For example, in order to acquire a CT image, the CT apparatus should perform an image reconstruction operation by using the raw data acquired by CT imaging.

SUMMARY

In the case of an X-ray, because it is transmitted from a transmitter through an object to a receiver, physical attenuation may occur therein. Due to such attenuation and scattering phenomena, when a tomography image is generated by using the X-ray acquired by the receiver, the resolution thereof may degrade, and when a user uses the generated tomography image, a clear diagnosis of the object may be difficult.

Provided are tomography apparatuses and methods for reconstructing a tomography image thereof, which may reconstruct a high-resolution tomography image.

Additional aspects will be set forth in part in the description which follows and, in part, will be apparent from the description, or may be learned by practice of the presented exemplary embodiments.

According to a first aspect of an exemplary embodiment, a tomography method for generating a computed tomography (CT) image includes generating a first tomography image based on first raw data corresponding to a received X-ray comprising acquired photons; determining second raw data by generating a second tomography image having an increased resolution in comparison with the first tomography image and performing forward projection on the second tomography image; determining third raw data based on a first parameter, the first raw data, and the second raw data; and generating a third tomography image based on the third raw data, wherein the determining of the third raw data may be based on information about a distribution of the acquired photons, the information being included in at least one from among the first raw data and the second raw data.

The third raw data may have a same data amount as the first raw data; and the data amount may be based on a number of the acquired photons.

The determining of the third raw data may include determining a third matrix including the third raw data using a first matrix including the first raw data and a second matrix representing the first parameter, and the determining of the third raw data may be based on a difference between the third raw data and the second raw data.

The determining of the third raw data may include determining a third matrix including the third raw data by using a first matrix including the first raw data and a second matrix representing the first parameter; the determining of the third raw data may be based on a difference between the third raw data and the second raw data; the third raw data may have a same data amount as the first raw data; and the first matrix and the third matrix may have different sizes.

The tomography may further include acquiring a fourth tomography image by performing backward projection on the third raw data; and determining refined second raw data by performing forward projection on the fourth tomography image.

The determining of the third raw data may include: determining a second parameter representing an expected value of the third raw data; and determining the third raw data by using the first raw data and the second parameter.

The tomography method may further include: generating a changed second parameter; and determining a new third raw data using the changed second parameter, wherein the changed second parameter maximizes a similarity between the new third raw data and the first raw data.

The second tomography image may have the increased resolution in comparison with the first tomography image in an arrangement direction of a detector cell detecting the X-ray.

The received X-ray may be acquired by performing tomography on an object using a plurality of views; the second tomography image may have the increased resolution in comparison with the first tomography image in a view direction of at least one view from among the plurality of views.

The second tomography image may have the increased resolution in comparison with the first tomography image in the view direction and an arrangement direction of a detector cell detecting the X-ray.

According to another aspect of an exemplary embodiment, a tomography apparatus for generating a tomography image includes a receiver configured to receive first raw data corresponding to a received X-ray comprising acquired photons; and a processor configured to generate a first tomography image based on the first raw data, determine second raw data by generating a second tomography image having an increased resolution in comparison with the first tomography image and performing forward projection on the second tomography image, determine third raw data based on a first parameter, the first raw data, and the second raw data, and generate a third tomography image based on the third raw data, wherein the processor may be further configured to determine the third raw data based on information about the distribution of the acquired photons, the information being included in at least one from among the first raw data and the second raw data.

The third raw data may have a same data amount as the first raw data; and the data amount may be based on a number of the acquired photons.

The processor may be further configured to determine a third matrix including the third raw data using a first matrix including the first raw data and a second matrix representing the first parameter; the processor may be further configured to determine the third raw data based on a difference between the third raw data and the second raw data; and the first matrix and the third matrix may have different sizes.

The processor may be further configured to determine a third matrix including the third raw data using a first matrix including the first raw data and a second matrix representing the first parameter; the processor may be further configured to determine the third raw data based on a difference between the third raw data and the second raw data; the third raw data may have a same data amount as the first raw data; and the first matrix and the third matrix may have different sizes.

The processor may be further configured to acquire a fourth tomography image by performing backward projection on the third raw data and determines refined second raw data by performing forward projection on the fourth tomography image.

The processor may be further configured to determine a second parameter representing an expected value of the third raw data, and to determine the third raw data by using the first raw data and the second parameter.

The processor may be further configured to: generate a changed second parameter; and determine a new third raw data by using the changed second parameter; wherein the changed second parameter maximizes a similarity between the new third raw data and the first raw data.

The second tomography image may have the increased resolution in comparison with the first tomography image in a direction of arrangement of a detector cell detecting the X-ray.

The received X-ray may be acquired by performing tomography on an object using a plurality of views; the second tomography image may have the increased resolution in comparison with the first tomography image in a view direction of at least one view from among the plurality of views.

According to yet another aspect of an exemplary embodiment, a non-transitory computer-readable recording medium may be configured to store instructions thereon, the instructions including a program which, when executed by a processor, cause the processor to perform the methods described herein.

According to a further aspect of an exemplary embodiment, a method of generating a tomography image includes receiving an X-ray; generating a first tomography image based on the received X-ray, the first tomography image having a first resolution; generating first raw data from the first tomography image; generating a second tomography image from the first tomography image, the second tomography image having a second resolution higher than the first resolution; generating second raw data by performing forward projection on the second tomography image; generating third raw data using a parameter, the first raw data, and the second raw data; generating a third tomography image based on the third raw data; wherein the parameter may be determined based on statistical characteristics associated with at least one from among the first raw data and the second raw data.

The statistical characteristics may relate to an amount of photons collected during the receiving of the X-ray.

The generating of the second tomography image may include performing interpolation on the first tomography image.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
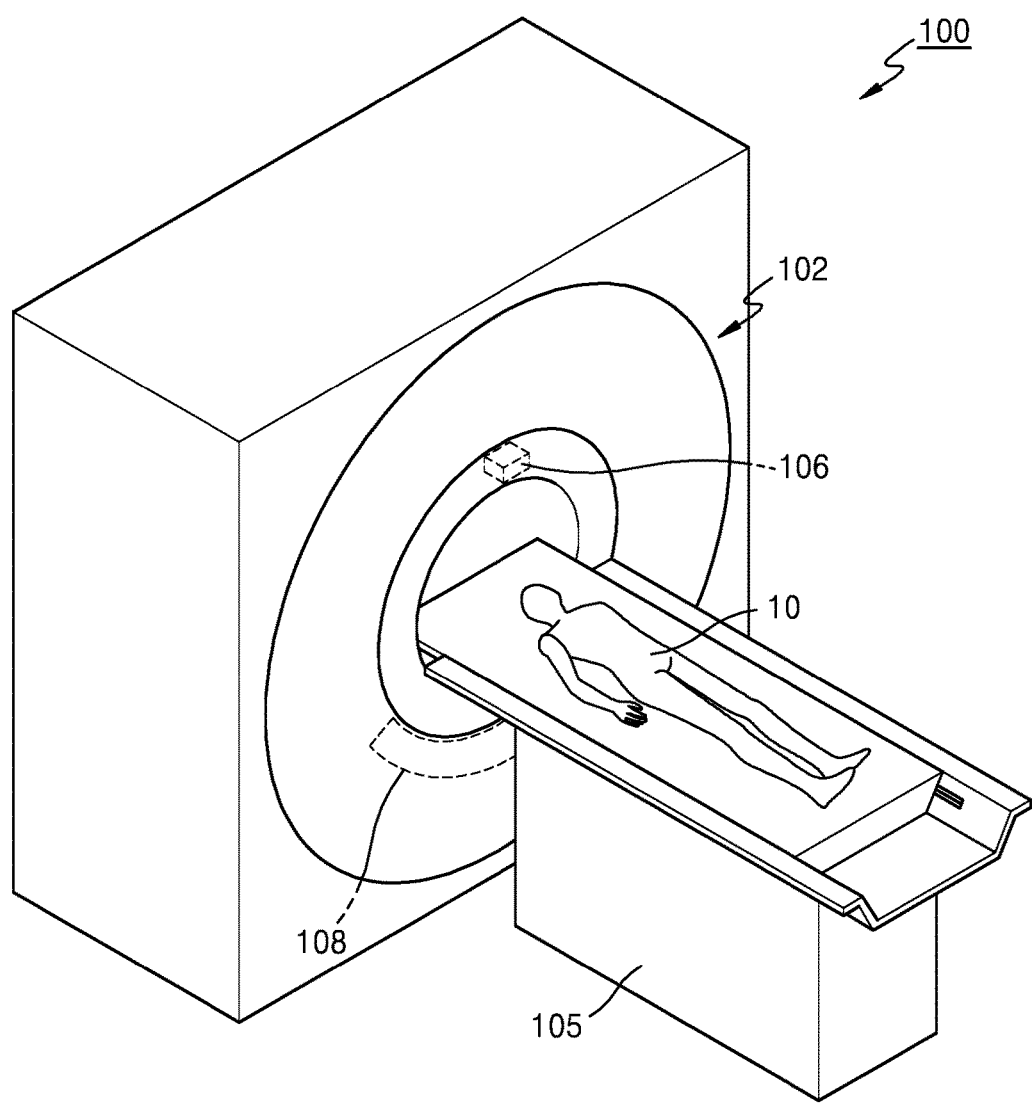
FIG. 1 is a schematic diagram of a general computed tomography (CT) system 100.

Reference will now be made in detail to exemplary embodiments, examples of which are illustrated in the accompanying drawings, wherein like reference numerals refer to like elements throughout. In this regard, exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The attached drawings for illustrating exemplary embodiments are referred to in order to gain a sufficient understanding of exemplary embodiments, the merits thereof, and the objectives accomplished by the implementation of exemplary embodiments. Exemplary embodiments may, however, be embodied in many different forms and should not be construed as being limited to the exemplary embodiments set forth herein; rather, these exemplary embodiments are provided such that this disclosure will be thorough and complete, and will fully convey exemplary embodiments to one of ordinary skill in the art. Like reference numerals refer to like elements throughout the specification.

The terms used in the specification will be briefly described, and then exemplary embodiments will be described in detail.

The terms used in this specification are those general terms currently widely used in the art in consideration of functions in regard to exemplary embodiments, but the terms may vary according to the intention of those of ordinary skill in the art, precedents, or new technology in the art. Also, specified terms may be selected by the applicant, and in this case, the detailed meaning thereof will be described in the detailed description. Thus, the terms used in the specification should be understood not as simple names but based on the meaning of the terms and the overall description.

When something "comprises" or "includes" a component, another component may be further included unless specified otherwise. Also, the term "unit" used herein means a software component or a hardware component such as a field-programmable gate array (FPGA) or an application-specific integrated circuit (ASIC), and performs some functions. However, the term "unit" is not limited to software or hardware. The "unit" may be formed so as to be in an addressable storage medium, or may be formed so as to operate one or more processors. Thus, for example, the "unit" may include components such as software components, object-oriented software components, class components, and task components, and may include processes, functions, attributes, procedures, subroutines, segments of program code, drivers, firmware, micro codes, circuits, data, a database, data structures, tables, arrays, and variables. A function provided by the components and "units" may be associated with the smaller number of components and "units", or may be divided into additional components and "units".

Reference will now be made in detail to exemplary embodiments, examples of which are illustrated in the accompanying drawings. In this regard, exemplary embodiments may have different forms and should not be construed as being limited to the descriptions set forth herein. While describing one or more exemplary embodiments, descriptions about drawings that are not related to the one or more exemplary embodiments are omitted for conciseness.

Throughout the specification, an "image" may mean multi-dimensional data formed of discrete image elements (e.g., pixels in a two-dimensional (2D) image and voxels in a three-dimensional (3D) image). For example, the image may include a medical image of an object which is acquired by a computed tomography (CT) imaging apparatus.

Throughout the specification, a "CT image" may mean an image generated by synthesizing a plurality of X-ray images that are acquired by imaging an object while a CT imaging apparatus rotates around at least one axis with respect to the object.

Throughout the specification, an "object" may include a human, an animal, or a portion or all of a human or animal. For example, the object may include at least one of a blood vessel and an organ such as a liver, a heart, a womb, a brain, a breast, or an abdomen. Also, the object may include a phantom. The phantom may refer to a material having a volume that is very close to a density and effective atomic number of an organism, and may include a spherical phantom having a characteristic similar to a physical body.

Throughout the specification, a "user" may include, but is not limited to, a medical expert such as a doctor, a nurse, a medical laboratory technologist, or a medical image expert, or a technician who repairs a medical apparatus.

Because a CT system is capable of providing a cross-sectional image of an object, the CT system may express an internal structure (e.g., an organ such as a kidney or a lung) of the object without an overlap therebetween, compared to a general X-ray imaging apparatus.

For example, the CT system may acquire image data with a thickness of not more than 2 mm, several tens to several hundreds of times per second, and process the acquired image data to provide a relatively accurate cross-sectional image of the object. According to related art, only a horizontal cross-sectional image of the object may be acquired, but this issue has been overcome due to various image reconstruction methods. Examples of 3D image reconstruction methods include the following.

- A shade surface display (SSD) method: The SSD method is an initial 3D imaging method that displays only voxels having a predetermined Hounsfield Units (HU) value.
- A maximum intensity projection (MIP)/minimum intensity projection (MinIP) method: The MIP/MinIP method is a 3D imaging method that displays only voxels having the greatest or smallest HU value among voxels constituting an image.
- A volume rendering (VR) method: The VR method is an imaging method capable of adjusting a color and transmittance of voxels constituting an image, according to regions of interest.
- A virtual endoscopy method: This method allows an endoscopic observation in a 3D image that is reconstructed by the VR method or the SSD method.

A multi-planar reformation (MPR) method: The MPR method is used to reconstruct an image into a different cross-sectional image. A user may reconstruct an image in every desired direction.

An editing method: This method involves editing adjacent voxels so as to allow a user to easily observe a region of interest in volume rendering (VR).

A voxel of interest (VOI) method: The VOI method displays only a selected region in volume rendering (VR).

A CT system 100 according to an exemplary embodiment will be described with reference to FIGS. 1 and 2. The CT system 100 may include various types of devices.

FIG. 1 is a schematic diagram of a CT system 100. Referring to FIG. 1, the CT system 100 may include a gantry 102, a table 105, an X-ray generator 106, and an X-ray detector 108.

The gantry 102 may include the X-ray generator 106 and the X-ray detector 108.

An object 10 may be located on the table 105.

The table 105 may move in a predetermined direction (e.g., at least one of up, down, right, and left directions) during a CT imaging process. Also, the table 105 may tilt or rotate by a predetermined angle in a predetermined direction.

The gantry 102 may also tilt by a predetermined angle in a predetermined direction.

Figure 2:
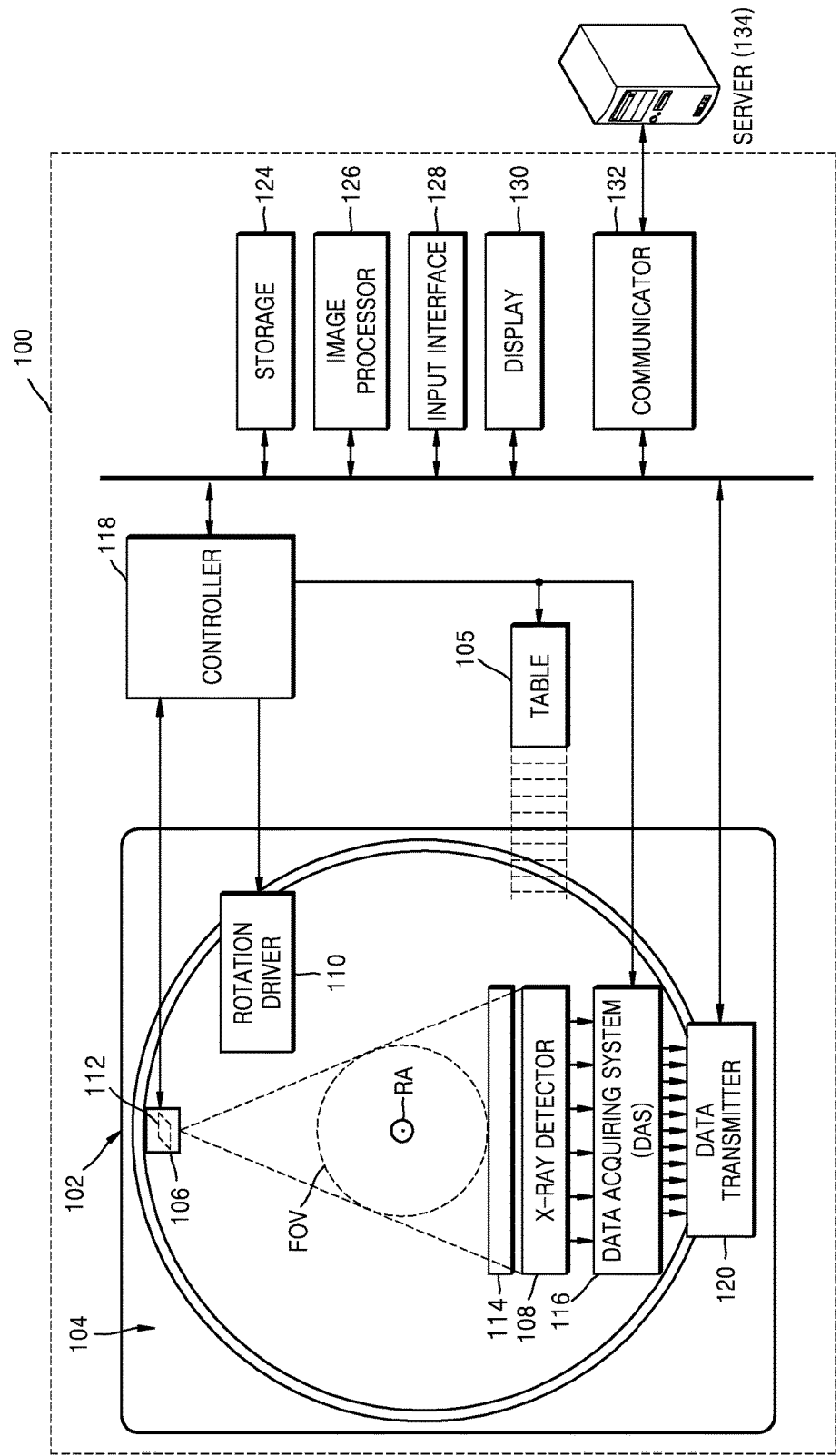
FIG. 2 is a diagram illustrating a structure of a CT system 100 according to an exemplary embodiment.

FIG. 2 is a diagram illustrating a structure of a CT system 100 according to an exemplary embodiment.

Referring to FIG. 2, the CT system 100 may include a gantry 102, a table 105, a controller 118, a storage 124, an image processor 126, an input interface 128, a display 130, and a communicator 132.

As described above, the object 10 may be located on the table 105. According to an exemplary embodiment, the table 105 may move in a predetermined direction (e.g., at least one of up, down, right, and left directions), and the movement of the table 105 may be controlled by the controller 118.

According to an exemplary embodiment, the gantry 102 may include a rotating frame 104, an X-ray generator 106, an X-ray detector 108, a rotation driver 110, a data acquisition system (DAS) 116, and a data transmitter 120.

According to an exemplary embodiment, the gantry 102 may include the rotating frame 104 having a loop shape capable of rotating with respect to a predetermined rotation axis RA. Also, the rotating frame 104 may have a disk shape.

The rotating frame 104 may include the X-ray generator 106 and the X-ray detector 108 facing each other so as to have a predetermined field of view FOV. Also, the rotating frame 104 may include an anti-scatter grid 114. The anti-scatter grid 114 may be located between the X-ray generator 106 and the X-ray detector 108.

In a medical imaging system, X-ray radiation that reaches a detector (or a photosensitive film) includes not only attenuated primary radiation that forms a useful image, but also includes scattered radiation that degrades the quality of an image. In order to transmit the primary radiation and to attenuate the scattered radiation, the anti-scatter grid 114 may be located between a patient and the detector (or the photosensitive film).

For example, the anti-scatter grid 114 may be formed by alternately stacking lead foil strips and interspace materials such as solid polymer materials, solid polymers, or fiber composite materials. However, the formation of the anti-scatter grid 114 is not limited thereto.

The rotating frame 104 may receive a driving signal from the rotation driver 110 and may rotate the X-ray generator 106 and the X-ray detector 108 at a predetermined rotation speed. The rotating frame 104 may receive the driving signal and power from the rotation driver 110 while the rotating frame 104 contacts the rotation driver 110 through a slip ring (not illustrated). Also, the rotating frame 104 may receive the driving signal and power from the rotation driver 110 through wireless communication.

The X-ray generator 106 may receive a voltage and current from a power distribution unit (PDU) (not illustrated) through a slip ring (not illustrated) and then a high voltage generator (not illustrated) to generate and emit an X-ray. When the high voltage generator applies a predetermined voltage (hereinafter referred to as a tube voltage) to the X-ray generator 106, the X-ray generator 106 may generate X-rays having a plurality of energy spectrums that correspond to the tube voltage.

The X-ray generated by the X-ray generator 106 may be emitted in a predetermined form by a collimator 112.

The X-ray detector 108 may be located to face the X-ray generator 106. The X-ray detector 108 may include a plurality of X-ray detecting devices. Each of the plurality of X-ray detecting devices may establish one channel, but exemplary embodiments are not limited thereto.

The X-ray detector 108 may detect the X-ray that is generated by the X-ray generator 106 and then transmitted through the object 10, and may generate an electrical signal corresponding to the intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. The electrical signal generated by the X-ray detector 108 may be collected by the DAS 116. The electrical signal generated by the X-ray detector 108 may be wiredly or wirelessly collected by the DAS 116. Also, the electrical signal generated by the X-ray detector 108 may be provided to an analog-to-digital converter through an amplifier.

According to a slice thickness or the number of slices, only some of data collected from the X-ray detector 108 may be provided to the image processor 126, or the image processor 126 may select only some of the data.

The digital signal may be provided to the image processor 126 through the data transmitter 120. The digital signal may be wiredly or wirelessly transmitted to the image processor 126 through the data transmitter 120.

According to an exemplary embodiment, the controller 118 may control an operation of each module in the CT system 100. For example, the controller 118 may control operations of the table 105, the rotation driver 110, the collimator 112, the DAS 116, the storage 124, the image processor 126, the input interface 128, the display 130, and/or the communicator 132.

The image processor 126 may receive data (e.g., pure data before a processing operation), which is acquired from the DAS 116, through the data transmitter 120 and perform preprocessing thereon.

For example, the preprocessing may include a process of correcting sensitivity irregularity between channels and a process of correcting a signal loss due to a rapid decrease of signal strength or due to an X-ray absorber such as metal.

Data output from the image processor 126 may be referred to as raw data or projection data. For example, the projection data and imaging conditions (e.g., the tube voltage and an imaging angle) during the acquisition of the data may be stored together in the storage 124.

The projection data may be a set of data values corresponding to the intensity of the X-ray that passes through the object 10. For convenience of description, a set of projection data acquired simultaneously from all channels at a same imaging angle will be referred to as a projection data set.

The storage 124 may include, for example, at least one storage medium among a flash memory-type storage medium, a hard disk-type storage medium, a multimedia card micro-type storage medium, a card-type memory (e.g., a secure digital (SD) memory or an extreme digital (XD) memory), a random-access memory (RAM), a static RAM (SRAM), a read-only memory (ROM), an electrically erasable programmable ROM (EEPROM), a programmable ROM (PROM), a magnetic memory, a magnetic disk, and an optical disk.

Also, the image processor 126 may reconstruct a cross-sectional image of the object 10 by using the projection data set. The cross-sectional image may be a 3D image. In other words, for example, the image processor 126 may reconstruct the 3D image of the object 10 based on the projection data set by using a cone beam reconstruction method.

For example, the input interface 128 may receive an external input with respect to an X-ray tomography condition or an image processing condition. For example, the X-ray tomography condition may include a plurality of tube voltages, an energy value setting with respect to a plurality of X-rays, a selection of an imaging protocol, a selection of an image reconstruction method, a setting of an FOV region, the number of slices, a slice thickness, or a parameter setting with respect to image postprocessing. Also, for example, the image processing condition may include the resolution of an image, attenuation coefficient setting with respect to the image, and/or setting of an image combination ratio.

The input interface 128 may include, for example, a device for receiving a predetermined input from an external source. For example, the input interface 128 may include a microphone, a keyboard, a mouse, a joystick, a touch pad, a touch pen, a voice recognition device, or a gesture recognition device.

The display 130 may display an X-ray tomography image reconstructed by the image processor 126.

For example, the exchange of data or power between the above elements may be performed by using at least one of wired communication, wireless communication, and optical communication.

For example, the communicator 132 may perform communication with an external device or an external medical apparatus through a server 134. Exemplary embodiments of the communication will be described below with reference to FIG. 3.

Figure 3:
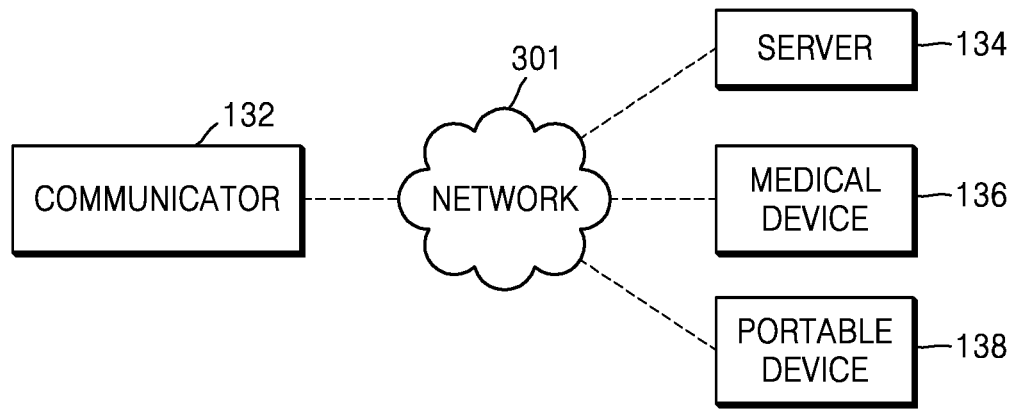
FIG. 3 is a diagram illustrating a configuration of a communicator.

FIG. 3 is a diagram illustrating a configuration of the communicator 132.

The communicator 132 may be wiredly or wirelessly connected to a network 301 to perform communication with an external server 134, a medical apparatus 136, or a portable device 138. The communicator 132 may exchange data with a hospital server or other medical apparatuses in a hospital connected through a Picture Archiving and Communication System (PACS).

Also, for example, the communicator 132 may perform data communication with the portable device 138 according to a Digital Imaging and Communications in Medicine (DICOM) standard.

The communicator 132 may transmit and receive data related to diagnosing the object 10, through the network 301. Also, for example, the communicator 132 may transmit and receive a medical image acquired from the medical apparatus 136 such as a magnetic resonance imaging (MRI) apparatus or an X-ray apparatus.

Also, for example, the communicator 132 may receive a diagnosis history or a medical treatment schedule about a patient from the server 134 and may use the diagnosis history or the medical treatment schedule in a clinical diagnosis for the patient. Also, for example, the communicator 132 may perform data communication not only with the server 134 or the medical apparatus 136 in a hospital but also with the portable device 138 of a user or patient.

Also, for example, the communicator 132 may transmit information about a device error or information about a quality control status to a system manager or a service manager through the network 301 and may receive a feedback corresponding to the information.

Figure 4:
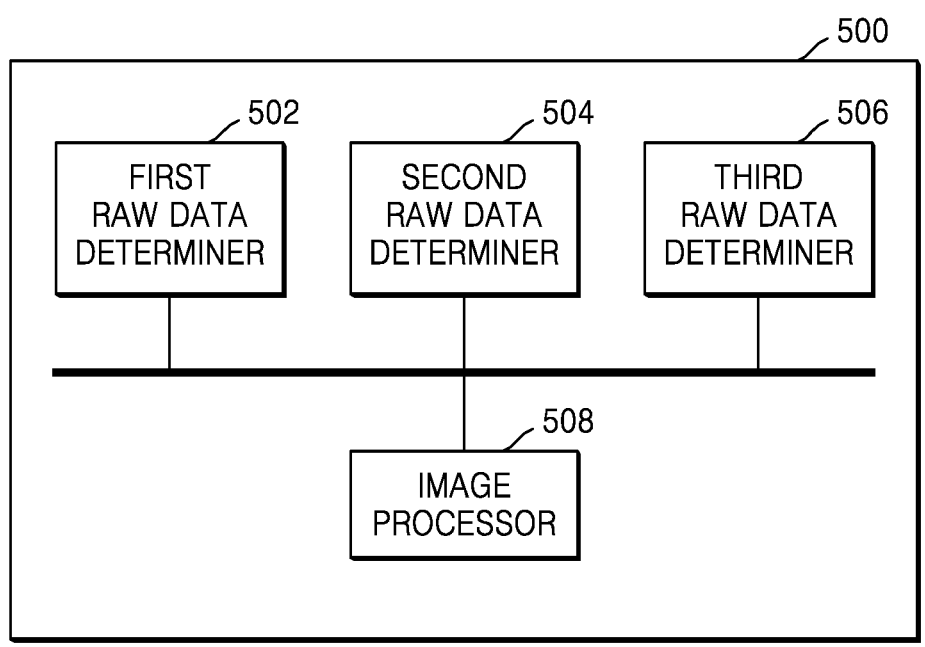
FIG. 4 is a block diagram of a tomography apparatus according to an exemplary embodiment.

FIG. 4 is a block diagram of a tomography apparatus 500 according to an exemplary embodiment.

Specifically, according to an exemplary embodiment, the tomography apparatus 500 may include a first raw data determiner 502, a second raw data determiner 504, a third raw data determiner 506, and an image processor 508. According to an exemplary embodiment, the image processor 508 may generate a high-resolution tomography image based on the raw data determined by the first raw data determiner 502, the second raw data determiner 504, and the third raw data determiner 506. The tomography method performed by the tomography apparatus 500 will be described below with reference to particular exemplary embodiments. According to an exemplary embodiment, the tomography apparatus 500 may include a receiver that receives a first raw data related to the received X-ray from data acquiring system 116.

Figure 5:
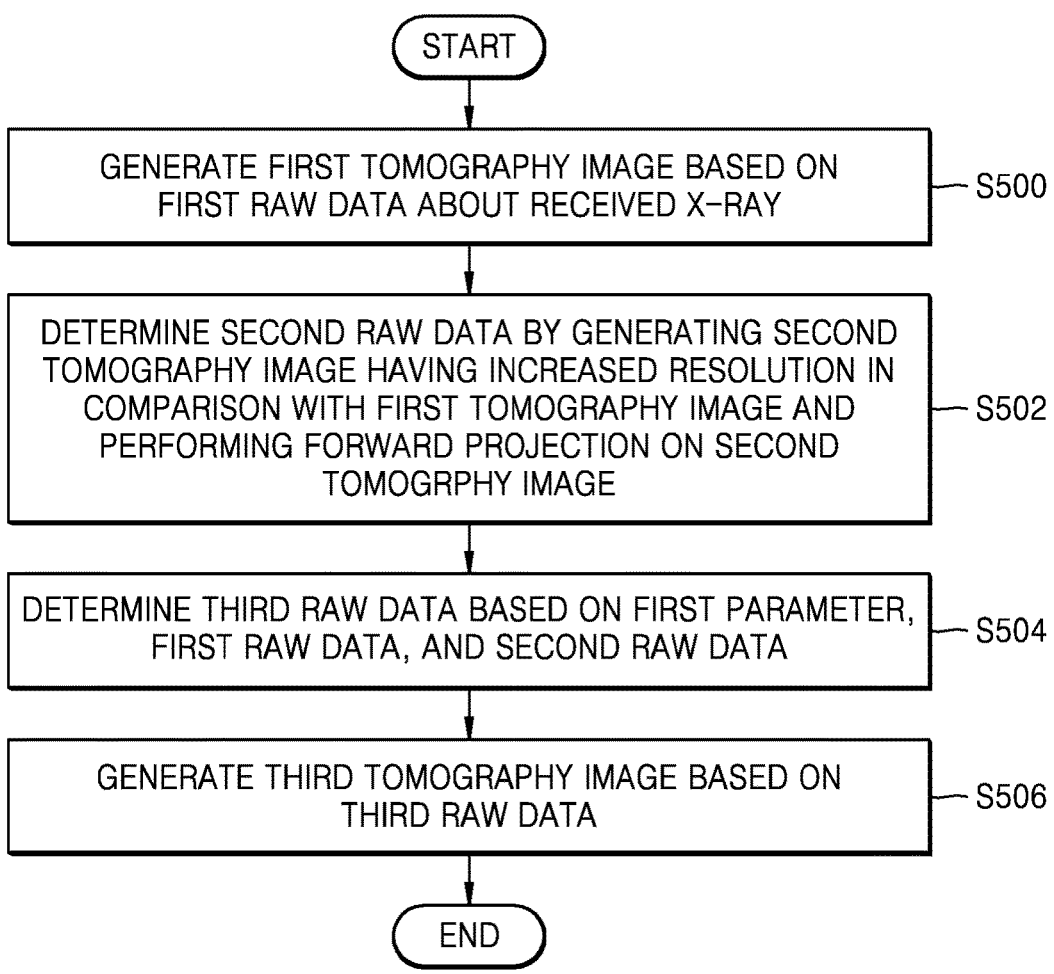
FIG. 5 is a flow diagram illustrating a tomography method performed by a tomography apparatus according to an exemplary embodiment.

FIG. 5 is a flow diagram illustrating a tomography method performed by the tomography apparatus 500 according to an exemplary embodiment.

In operation S500, according to an exemplary embodiment, the first raw data determiner 502 of the tomography apparatus 500 may generate a first tomography image based on the first raw data about a received X-ray. According to an exemplary embodiment, the first tomography image may be generated by using the first raw data about the X-ray information detected actually by a detector. That is, the tomography apparatus 500 may determine the first raw data by using information about the X-ray, which has passed through an object, by using the detector, and the image processor 508 may generate the first tomography image by using the determined first raw data. For example, the image processor 508 may generate the first tomography image by performing back projection or filtered back projection on the first raw data determined based on the acquired X-ray information. Herein, the detector of the tomography apparatus 500 may correspond to any device capable of detecting an X-ray, including the X-ray detector 108 of FIG. 2. Also, the operations of the first raw data determiner 502, the second raw data determiner 504, the third raw data determiner 506, and the image processor 508 may be performed by separate hardware or may be performed by single hardware (e.g., processor or CPU). According to an exemplary embodiment, the tomography apparatus 500 may include a processor that may perform the operations of the first raw data determiner 502, the second raw data determiner 504, the third raw data determiner 506, and the image processor 508.

Figure 6:
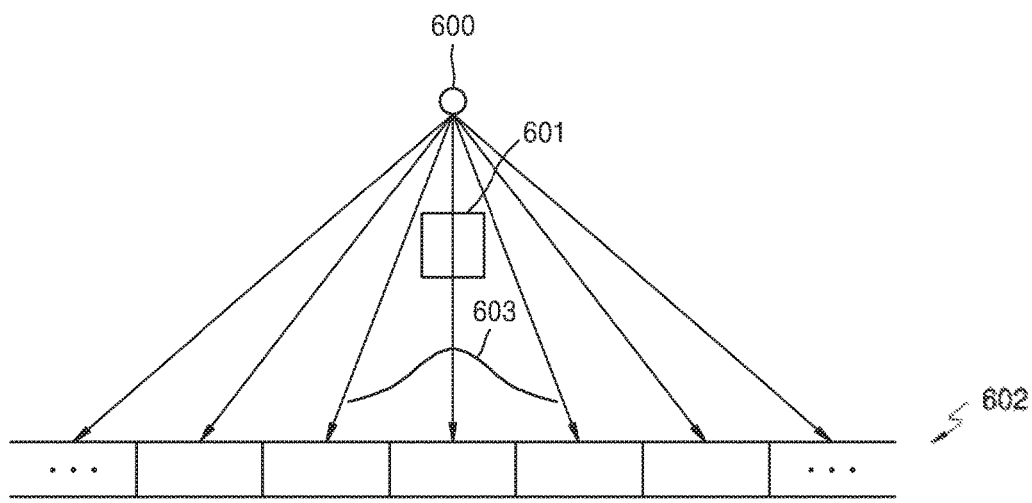
FIG. 6 illustrates a process of receiving an X-ray, which has passed through an object, by a tomography apparatus according to an exemplary embodiment.

FIG. 6 illustrates a process of receiving an X-ray, which has passed through an object, by the tomography apparatus 500 according to an exemplary embodiment.

According to an exemplary embodiment, the tomography apparatus 500 may receive, through a detector 602, an X-ray that has passed through an object 601 after being transmitted from an X-ray generator 600. Information about the X-ray detected by the detector 602 may include information about the distribution of photons detected by each of at least one detector cell included in the detector 602. For example, referring to FIG. 6, as the information about the X-ray, the tomography apparatus 500 may acquire information about photons 603 received in a particular distribution through the detector 602. The detector 602 of the tomography apparatus 500 may include a limited number of detector cells, and the tomography apparatus 500 may determine the raw data based on the X-ray information acquired by using the detector cells. However, when the raw data is determined by directly using the acquired X-ray information, the tomography image generated by using only the determined raw data may have a limited resolution according to the performance of the detector 602. For example, in order to generate a high-resolution tomography image by improving the resolution of the tomography image, related art uses a sharp filter or uses a method of increasing an X-ray sampling rate. However, related art methods have a problem such as a noise increase, a ringing artifact increase, or an SNR decrease. Hereinafter, a process of performing a tomography method will be described in detail as an exemplary embodiment for generating a high-resolution tomography image by using the X-ray distribution characteristics acquired directly through the detector 602.

In operation S502, according to an exemplary embodiment, the second raw data determiner 504 of the tomography apparatus 500 may determine second raw data by performing forward projection on the first tomography image.

According to an exemplary embodiment, the second raw data determiner 504 of the tomography apparatus 500 may determine the second raw data simulated by using the first tomography image generated in operation S500. Like the first raw data used in operation S500, the second raw data determined as a result of the forward projection may include information about photons representing a particular distribution. However, in this case, since the second raw data is not the raw data generated by directly irradiating and detecting the X-ray with respect to the object and corresponds to the raw data simulated based on the generated tomography image, it may be determined through a different process than the first raw data.

According to an exemplary embodiment, the second raw data determiner 504 may increase the resolution of the first tomography image and then perform forward projection on a second tomography image having an increased resolution in comparison with the first tomography image. For example, the second raw data determiner 504 may generate the second tomography image having an increased resolution in comparison with the first tomography image by performing interpolation on the first tomography image and generate the second raw data by performing forward projection on the generated second tomography image.

In operation S504, according to an exemplary embodiment, the tomography apparatus 500 may determine third raw data based on a first parameter, the first raw data, and the second raw data.

According to an exemplary embodiment, the third raw data determiner 506 of the tomography apparatus 500 may determine the third raw data about a tomography image having an improved resolution in comparison with the first tomography image based on the first parameter, the first raw data determined by the first raw data determiner 502, and the second raw data determined by the second raw data determiner 504.

According to an exemplary embodiment, in order to determine the third raw data, the tomography apparatus 500 may use information about the distribution of acquired photons represented by the first raw data and the second raw data. Specifically, as information about the distribution of photons acquirable according to the first raw data and the second raw data, the tomography apparatus 500 may use statistical characteristics represented by the distribution of photons acquired by at least one detector cell included in the detector 602. In order to acquire the third raw data by using the statistical characteristics, the tomography apparatus 500 may use a method of finding a maximum a posteriori (MAP) as the third raw data on the assumption that at least one parameter used in an expectation-maximization (EM) algorithm has a predetermined value. At least one parameter used in the EM algorithm may include information about the number of photons detected actually by the tomography apparatus 500. A Bayes' theorem may be used as the method of finding the MAP.

According to an exemplary embodiment, the tomography apparatus 500 may determine the third raw data by using statistical characteristics about at least one of the first raw data and the second raw data.

According to an exemplary embodiment, the first parameter usable by the third raw data determiner 506 of the tomography apparatus 500 may represent the relationship between the first raw data and the third raw data. For example, the first raw data including information about the received X-ray may be represented in the form of a matrix, and the third raw data may also be represented in the form of a matrix. The relationship between a first matrix including the first raw data and a third matrix including the third raw data may be determined based on the first parameter. Herein, the matrix including the raw data may include information about the amount of photons detected as information about the X-ray received by each detector cell.

According to an exemplary embodiment, the third raw data determiner 506 of the tomography apparatus 500 may determine a third matrix including the third raw data by using a first matrix including the first raw data and a second matrix representing the first parameter, and the first matrix and the third matrix may have different sizes. For example, the first matrix including the first raw data, the second matrix representing the first parameter, and the third matrix including the third raw data may be expressed as Equation 1 below.

$$I = Wz \qquad \text{Equation 1}$$

Herein, "I" may correspond to the first matrix including the first raw data, "W" may correspond to the second matrix representing the first parameter, "z" may correspond to the third matrix including the third raw data, and a matrix multiplication operation may be performed between the second matrix and the third matrix. According to an exemplary embodiment, by using the first parameter, the tomography apparatus 500 may process information about the X-ray detected by each detector cell included in a detector 702, which is represented by the first raw data, into information about the X-ray detected by each detector cell included in a virtual detector 704. Exemplary embodiments may be performed on the assumption that the total amount of information (e.g., amount of photons) about the X-ray acquired by the detector 702 does not change even when using the virtual detector 704. According to the first parameter, on the assumption that the total amount of the information about the X-ray is constant, information about the X-ray detected by each detector cell of the detector 702 may be divided at a predetermined ratio into information about the X-ray detected by the respective detector cells included in the virtual detector 704. The predetermined ratio may vary according to the objects and the imaging environments of the tomography apparatus 500, or may be predetermined as a ratio of a predetermined constant. For example, referring to FIG. 7, by using the first parameter, the tomography apparatus 500 may divide information about the X-ray detected by each detector cell of the detector 702 at a ratio of 1:2:1 into information about the X-ray detected by the respective detector cells included in the virtual detector 704. Since the size of a detector cell of the virtual detector 704 may be smaller than the size of a detector cell of the detector 702, information about the X-ray of a detector cell 720 (as the detector cell of the virtual detector 704) corresponding to the position of a detector cell 740 of the detector 702 (or located at a completely overlapping position therewith) may include ½ of the amount of information about the X-ray detected by the detector cell of the detector 702. Unlike this, information about the X-ray of a detector cell 710 or 730 not corresponding to the position of each detector cell of the detector 702 (or located at an incompletely overlapping position therewith) may include ¼ of the amount of information about the X-ray detected by the detector cell of the detector 702. Accordingly, the total amount of information about the X-ray determined to be detected by the detector cells 710, 720, and 730 of the virtual detector 704 may be equal to the total amount of information about the X-ray detected actually by the detector cell 740 of the detector 702.

According to an exemplary embodiment, the first raw data determiner 502 of the tomography apparatus 500 may determine the first raw data related to the X-ray acquired through a detector, and the second raw data determined by forward-projecting the first tomography image or the second raw data determined by forward-projecting the second tomography image having an increased resolution in comparison with the first tomography image may be used in order to generate a third tomography image having an increased resolution in comparison with the first tomography image that may be generated based on the determined first raw data. According to an exemplary embodiment, the size of the second matrix related to the second raw data may be equal to the size of the third matrix related to the third raw data.

According to an exemplary embodiment, the third raw data determiner 506 of the tomography apparatus 500 may determine the third raw data as raw data having the smallest difference from the second raw data. For example, the tomography apparatus 500 may determine the second raw data by forward-projecting the first tomography image, and the third raw data determiner 506 may determine the third raw data based on whether the second matrix and the third matrix are equal to each other, by comparing the second matrix including the second raw data and the third matrix including the third raw data, which have the same size. For example, in the process of determining the third raw data, the third raw data determiner 506 of the tomography apparatus 500 may determine the third matrix having a size determined based on the first matrix including the first raw data and the second matrix representing the first parameter, and may determine the third matrix as a matrix having the smallest difference from the second matrix. In this case, the third raw data determiner 506 may consider the amount of the first raw data before determining the third raw data. For example, the third raw data determiner 506 may determine the third matrix having a size determined based on the first matrix and the second matrix representing the first parameter, and may determine the third raw data having a data amount equal to the amount of the first raw data as a matrix having the smallest difference from the second raw data. Herein, the amount of the first raw data may be information corresponding to the number of photons related to the X-ray detected by the detector, and thus the third raw data determiner 506 may determine the third raw data on the assumption that the total amount of photons actually detected by the detector is constant.

Figure 7:
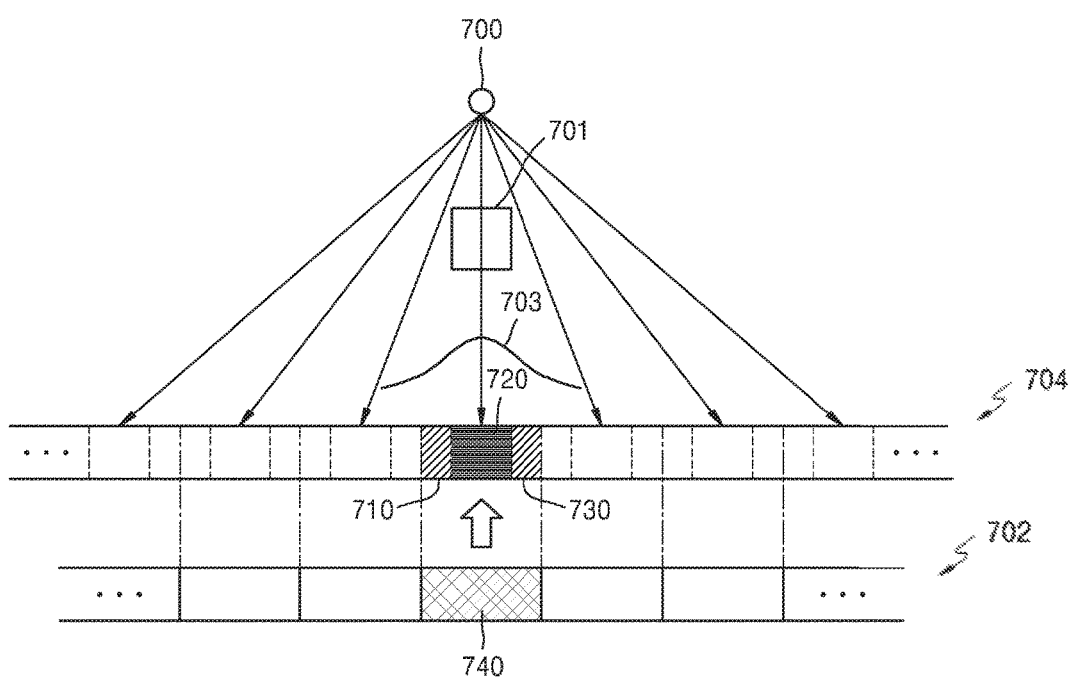
FIG. 7 illustrates a process of acquiring X-ray information necessary for tomography by a tomography apparatus by virtually dividing a detector acquiring an X-ray when tomographing an object according to an exemplary embodiment.

FIG. 7 illustrates a process of acquiring X-ray information necessary for tomography by the tomography apparatus 500 by virtually dividing a detector acquiring an X-ray when tomographing an object according to an exemplary embodiment.

According to an exemplary embodiment, the tomography apparatus 500 may acquire, through the detector 702, X-ray information that is received when an X-ray passes through an object 701 after being transmitted from an X-ray generator 700. The X-ray information acquired by each detector cell included in the detector 702 may include information about photons 703 received in a particular distribution. That is, the X-ray transmitted from the X-ray generator 700 is not received with a constant value in each detector cell included in the detector 702, but photons having a particular distribution such as a Gaussian distribution or a Poisson distribution are received in the detector cell. By analyzing the distribution of detected photons, the tomography apparatus 500 may generate a tomography image having an increased resolution in comparison with a tomography image based on the distribution of photons acquired by a limited number of detector cells included in the detector 702. For example, by analyzing the distribution of photons detected by the detector 702, the third raw data determiner 506 of the tomography apparatus 500 may derive the same result as detecting the X-ray information by using the virtual detector 704 including more detector cells than the detector 702. That is, a tomography image having a relatively high resolution may be generated when the first raw data determined according to the result of the detecting the X-ray by the detector 702 is used instead of the third raw data determined according to the result of the detecting the X-ray by the virtual detector 704.

Referring to FIG. 7, the size of detector cells of the detector 702 may correspond to two times of the size of detector cells of the virtual detector 704 that may be determined based on the distribution of photons, and the third raw data generated by using the detector cells of the virtual detector 704 may correspond to the result of increasing a sampling rate for tomography. Also, according to an exemplary embodiment, since the third raw data having the same data amount as the first raw data may be determined, a tomography result corresponding to the result of tomography may be acquired by increasing the sampling rate regardless of a change in the X-ray dose.

According to an exemplary embodiment, the tomography apparatus 500 may determine the third raw data as raw data having the smallest difference from the second raw data, when the third matrix including the third raw data is determined by using the first matrix including the first raw data and the second matrix representing the first parameter. Also, since the first matrix and the third matrix may have different sizes, the size of the first matrix may be determined based on the sizes of the second matrix and the third matrix in the relationship between the matrixes. Since the relationship between the sizes of the matrixes may correspond to the description of the above embodiment, detailed descriptions thereof will be omitted for conciseness. In order to determine the third raw data based on the first matrix, the second matrix, the third matrix, and the raw data having the smallest difference from the second raw data, the third raw data determiner 506 of the tomography apparatus 500 may use Equation 2 below.

$$z := \arg\min_{I=Wz}(z-\theta)^2 \qquad \text{Equation 2}$$

Herein, "I" may correspond to the first matrix including the first raw data, "W" may correspond to the second matrix representing the first parameter, "z" may correspond to the third matrix including the third raw data, and a matrix multiplication operation may be performed between the second matrix and the third matrix. Also, as a second parameter, "θ" may correspond to a matrix representing an expected value of the third raw data. That is, in the process of determining the third raw data for generating a high-resolution tomography image by using a virtual detector, the tomography apparatus 500 may use "θ" including an expected value of the amount of photons detected by each detector cell included in the virtual detector.

According to an exemplary embodiment, in order to determine an initial value of "θ", the tomography apparatus 500 may use, as the initial value of "θ", the second raw data acquired by forward-projecting the first tomography image generated by using the X-ray information acquired by the detector 702. That is, the second raw data determined based on the first raw data may be used to determine an initial value of the second parameter.

According to an exemplary embodiment, the tomography apparatus 500 may determine the second raw data by using the initial value of the second parameter and may update the second parameter based on the determined second raw data. According to an exemplary embodiment, through a process corresponding to an expectation step (E-step) in the EM (expectation-maximization) algorithm, the tomography apparatus 500 may determine the third raw data by using the initial value of the second parameter. Also, through a process corresponding to a maximization step (M-step), the tomography apparatus 500 may update the second parameter value by determining the second parameter value maximizing the third raw data determined in the expectation step. That is, through a method of determining the maximum likelihood, the tomography apparatus 500 may update the second parameter that is an expected value of the number of photons acquirable by at least one detector cell included in the virtual detector. Through the above process, the tomography apparatus 500 may determine the third raw data by using the second parameter having an initial value and may change the second parameter so that the third raw data has a maximum value. Accordingly, by determining the third raw data by using the changed second parameter, the tomography apparatus 500 may newly determine the third raw data that is more similar to the first raw data about the actually-acquired photons, than the third raw data determined by using the second parameter before the change.

According to an exemplary embodiment, the tomography apparatus 500 may acquire the second raw data by forward-projecting the first tomography image determined as the initial value of the second parameter and may change the second raw data by using the third raw data determined based on the first raw data and the initial value of the second parameter. This will be described below in detail with reference to various exemplary embodiments.

In operation S506, the tomography apparatus 500 may generate the third tomography image based on the third raw data determined in operation S504.

According to an exemplary embodiment, the image processor 508 of the tomography apparatus 500 may generate the third tomography image by using the third raw data, and the generated third tomography image may have an increased resolution in comparison with the first tomography image that may be generated by directly using the X-ray information acquired by the detector 702.

Figure 8:
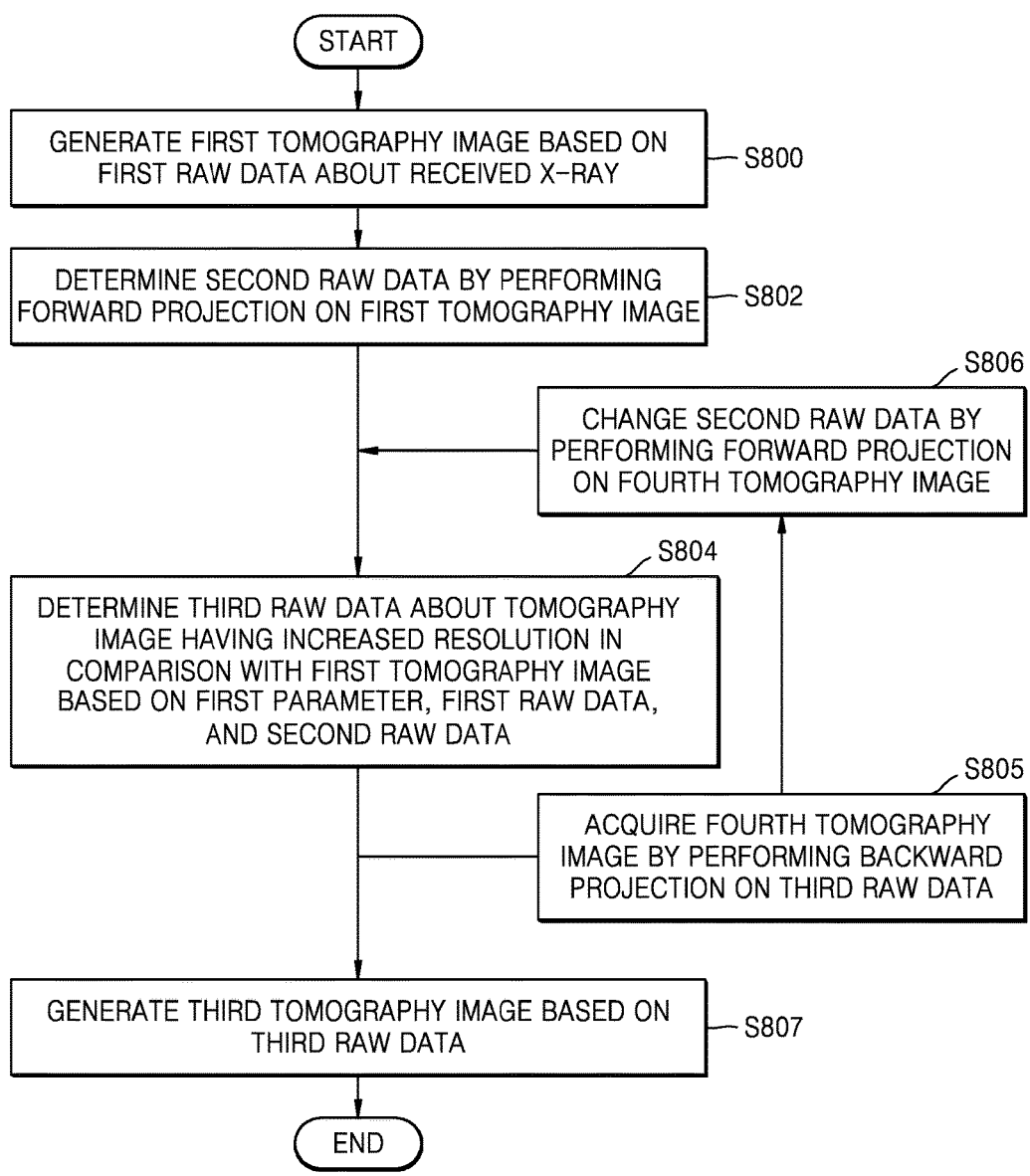
FIG. 8 is a flow diagram illustrating a process of updating second raw data by a tomography apparatus by using third raw data determined based on first raw data according to an exemplary embodiment.

FIG. 8 is a flow diagram illustrating a process of updating second raw data by the tomography apparatus 500 by using third raw data determined based on first raw data according to an exemplary embodiment.

In operation S800, according to an exemplary embodiment, the tomography apparatus 500 may generate a first tomography image based on the first raw data about a received X-ray. This may correspond to the description of operation S500 of FIG. 5, and thus detailed descriptions thereof will be omitted for conciseness.

In operation S802, according to an exemplary embodiment, the second raw data determiner 504 of the tomography apparatus 500 may determine second raw data by performing forward projection on the first tomography image. Because the second raw data determined in operation S802 is acquired by using the first raw data including information about the photons actually acquired by the tomography apparatus 500 through the detector 702 in operation S800, it has a different source from the second raw data changed based on a fourth tomography image described below with respect to operation S806. This may correspond to the description of operation S502 of FIG. 5, and thus detailed descriptions thereof will be omitted for conciseness.

In operation S804, according to an exemplary embodiment, the tomography apparatus 500 may determine third raw data based on a first parameter, the first raw data, and the second raw data. This may correspond to the description of operation S504 of FIG. 5, and thus detailed descriptions thereof will be omitted for conciseness.

In operation S805, according to an exemplary embodiment, the tomography apparatus 500 may acquire a fourth tomography image by performing backward projection on the third raw data determined in operation S804.

Specifically, when the fourth tomography image is acquired by backward-projecting the third raw data acquired by using only the first raw data acquired actually through the detector 702, the acquired fourth tomography image may represent the object more minutely and accurately than the second tomography image acquired by increasing the resolution of the first tomography image related to the first raw data (for example, by performing interpolation). However, in addition, in order to update the second raw data determined in operation S802 based on the third raw data, the image processor 508 of the tomography apparatus 500 may use the fourth tomography image acquired by backward-projecting the third raw data.

In operation S806, according to an exemplary embodiment, the tomography apparatus 500 may perform forward projection on the fourth tomography image determined in operation S805 and may change the second raw data determined in operation S802, based on the result of the forward projection.

According to an exemplary embodiment, the image processor 508 of the tomography apparatus 500 may acquire raw data about the fourth tomography image by forward-projecting the fourth tomography image. The tomography apparatus 500 may change the acquired raw data about the fourth tomography image into the second raw data determined in operation S802. That is, the second raw data acquired in operation S802 by performing forward projection on the first tomography image may be changed according to the result of the forward projection on the fourth tomography image in operation S806. Accordingly, when the third raw data is determined recursively based on the second raw data changed in operation S806, a tomography image capable of more minutely representing the object may be acquired based on the third raw data.

According to an exemplary embodiment, the third raw data determiner 506 of the tomography apparatus 500 may determine the third raw data based on the first parameter, the first raw data, and the second raw data. However, herein, the second raw data used by the tomography apparatus 500 may include the second raw data changed by using the raw data acquired by performing forward projection on the fourth tomography image in operation S806. That is, the image processor 508 of the tomography apparatus 500 may change the second raw data by using the result acquired by forward-projecting the fourth tomography image, and the third raw data determiner 506 may update the third raw data by determining the current third raw data as the new third raw data by using the changed second raw data, the first raw data, and the first parameter. Accordingly, by using the third raw data determined by using the changed second raw data, the image processor 508 of the tomography apparatus 500 may represent the object more minutely and clearly than the case of using the third raw data determined based on the second raw data before the change.

According to an exemplary embodiment, the tomography apparatus 500 may determine the new third raw data by using the first parameter, the first raw data, and the second raw data changed in operation S806, and may repeatedly perform operations S805 and S806 on the new third raw data determined. That is, the tomography apparatus 500 may recursively perform operations S805 and S806 for generating a higher-quality tomography image, and may determine the amount of photons acquirable by each of at least one detector cell included in the virtual detector 704, based on the new third raw data determined by the result of performing operations S805 and S806.

According to an exemplary embodiment, the tomography apparatus 500 may change the second raw data based on the result of the forward projection on the fourth tomography image and may change the second parameter representing the expected value of the third raw data based on the changed second raw data. The image processor 508 of the tomography apparatus 500 may change the second parameter representing the expected value of the third raw data based on the changed second raw data, and the third raw data determiner 506 may re-determine the third raw data by using the changed second parameter. Specifically, the image processor 508 of the tomography apparatus 500 may change the expected value of the third raw data based on the changed second parameter, and the third raw data determiner 506 may update the current third raw data by using the changed expected value of the third raw data.

According to an exemplary embodiment, by using the expected value of the third raw data, the third raw data determiner 506 of the tomography apparatus 500 may generate a tomography image having an improved image quality in comparison with the case of using the expected value of the third raw data before the update. That is, the tomography apparatus 500 may change the second parameter used in operation S804, by using the result of the forward projection on the fourth tomography image generated by the result of the backward projection on the third raw data determined in operation S804. Accordingly, the tomography apparatus 500 may generate a tomography image having an improved image quality by using the expected value of the new third raw data represented by the changed second parameter. A process of updating, by the tomography apparatus 500, the parameter used in operation S804 for generating the raw data by performing operations S805 and S806 based on the raw data acquired by using the acquired X-ray information may be considered as a statistical learning-based raw data generating method that may be used by the tomography apparatus 500. That is, a recursive tomography method for re-performing, by the tomography apparatus 500, operation S804 by performing operations S805 and S806 by using the third raw data determined in operation S804 may be considered as being based on a statistical learning technique.

Figure 9:
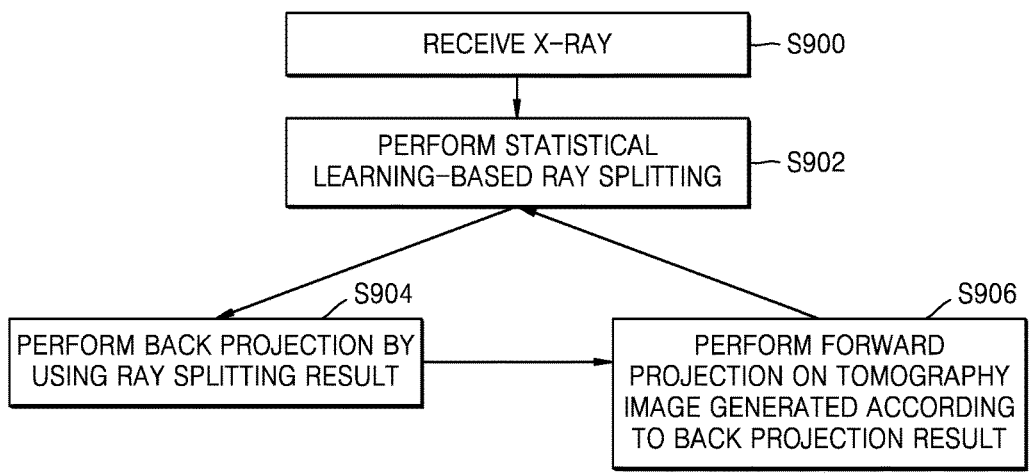
FIG. 9 illustrates a process of generating a tomography image of an improved image quality by using a statistical learning-based ray splitting process, as a tomography method performed by a tomography apparatus according to an exemplary embodiment.

FIG. 9 illustrates a process of generating a tomography image of an improved image quality by using a statistical learning-based ray splitting process, as a tomography method performed by the tomography apparatus 500 according to an exemplary embodiment.

In operation S900, according to an exemplary embodiment, the tomography apparatus 500 may acquire information about the X-ray detected through the detector 702. The acquired information about the X-ray may include information about the amount or number of photons detected by the detector 702.

In operation S902, the tomography apparatus 500 may perform a statistical learning-based ray splitting process. The statistical learning-based ray splitting process may be a process of generating raw data by using the virtual detector 704 including more detector cells than the number of at least one detector cell included in the detector 702 for X-ray detection, instead of generating raw data by the tomography apparatus 500 by directly using information about the X-ray detected actually through the detector 702. That is, the process performed in operation S902 may correspond to operation S804 of FIG. 8 that uses the first parameter, the first raw data, and the second raw data in order to determine the third raw data having an increased resolution in comparison with the raw data acquired through a back projection process by directly using the information about the X-ray acquired in operation S900.

That is, for statistical learning-based ray splitting, as information about the distribution of photons acquirable according to the first raw data and the second raw data, the tomography apparatus 500 may use statistical characteristics represented by the distribution of photons acquired by at least one detector cell included in the detector 702. That is, the statistical learning-based ray splitting process performed by the tomography apparatus 500 may include a process of finding a maximum a posteriori (MAP) by using a predetermined value of at least one parameter used in the expectation-maximization (EM) algorithm (EM-method) (for example, information about the X-ray detected actually through the detector 702 or the amount of actually-acquired photons).

According to an exemplary embodiment, the third raw data determiner 506 of the tomography apparatus 500 may determine a third matrix including the third raw data by using a first matrix including the first raw data and a second matrix representing the first parameter, and the first matrix and the third matrix may have different sizes. For example, the first matrix including the first raw data, the second matrix representing the first parameter, and the third matrix including the third raw data may be expressed as Equation 1 above.

According to an exemplary embodiment, the first raw data determiner 502 of the tomography apparatus 500 may determine the first raw data related to the X-ray acquired through the detector 702, and the second raw data determined by forward-projecting the first tomography image or the second tomography image having an increased resolution in comparison with the first tomography image may be used in order to generate a third tomography image having an increased resolution in comparison with the first tomography image that may be generated based on the determined first raw data. According to an exemplary embodiment, the size of the second matrix related to the second raw data may be equal to the size of the third matrix related to the third raw data.

According to an exemplary embodiment, the third raw data determiner 506 of the tomography apparatus 500 may determine the third raw data as raw data having the smallest difference from the second raw data. For example, the tomography apparatus 500 may determine the second raw data by forward-projecting the first tomography image, and the third raw data determiner 506 may determine the third raw data based on whether the second matrix and the third matrix are equal to each other, by comparing the second matrix including the second raw data and the third matrix including the third raw data, which have the same size. For example, in the process of determining the third raw data, the third raw data determiner 506 of the tomography apparatus 500 may determine the third matrix having a size determined based on the first matrix including the first raw data and the second matrix representing the first parameter, and may determine the third matrix as a matrix having the smallest difference from the second matrix. In this case, the third raw data determiner 506 may consider the amount of the first raw data before determining the third raw data. For example, the third raw data determiner 506 may determine the third matrix having a size determined based on the first matrix and the second matrix representing the first parameter, and may determine the third raw data having a data amount equal to the amount of the first raw data as a matrix having the smallest difference from the second raw data. Herein, the amount of the first raw data may be information corresponding to the number of photons related to the X-ray detected by the detector 702, and thus the third raw data determiner 506 may determine the third raw data on the assumption that the total amount of photons detected actually by the detector 702 is constant.

FIG. 7 illustrates a process of acquiring X-ray information necessary for tomography by the tomography apparatus 500 by virtually dividing a detector acquiring an X-ray when tomographing an object according to an exemplary embodiment.

Since a method of performing the statistical learning-based ray splitting process by the tomography apparatus 500 has been described above in detail with reference to FIG. 7 and operation S804 of FIG. 8, detailed descriptions thereof will be omitted herein for conciseness.

Figure 10A:
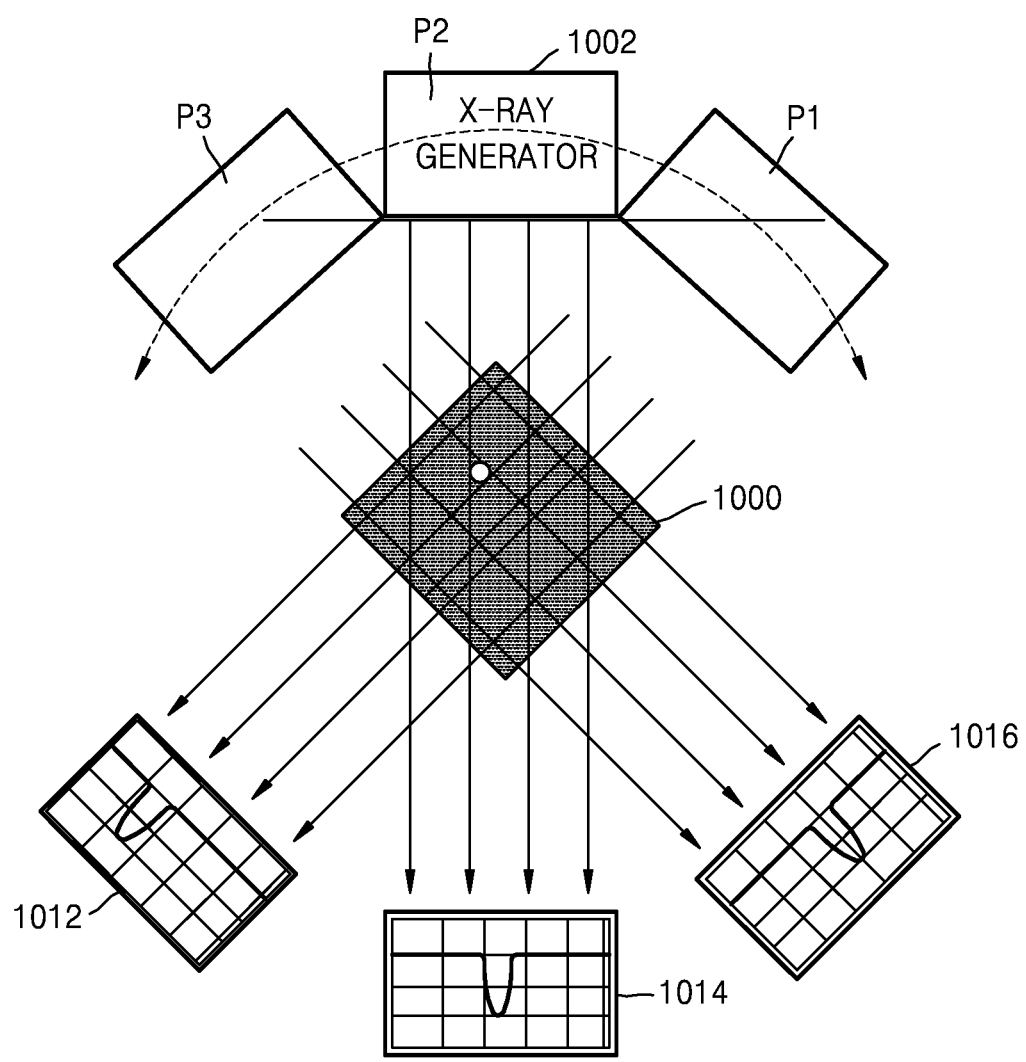
FIGS. 10A and 10B are diagrams illustrating exemplary embodiments of a tomography image and a reconstructing operation thereof.
Figure 10B:
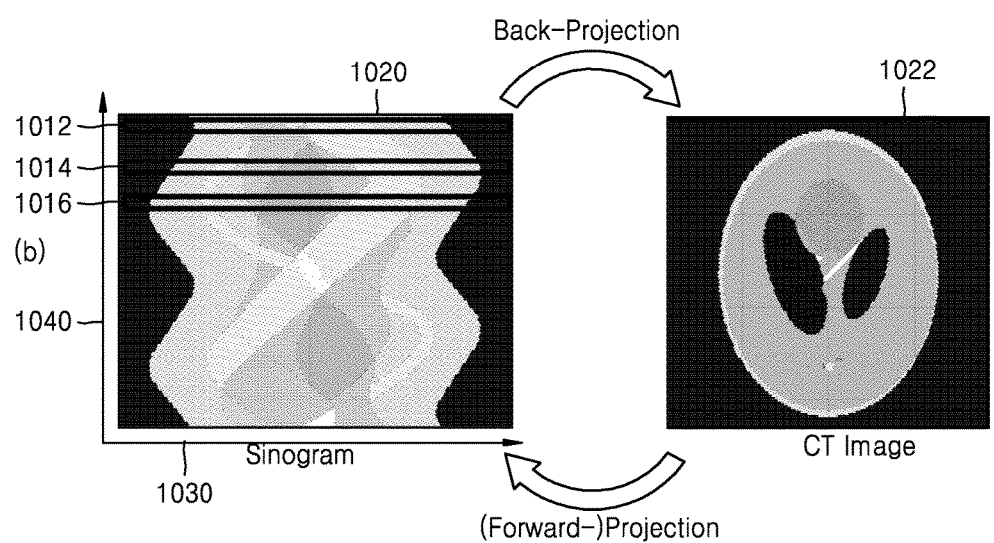

FIGS. 10A and 10B are diagrams illustrating a tomography image and a reconstructing operation thereof.

Specifically, FIG. 10A is a diagram illustrating a tomography operation of the tomography apparatus 500 that performs tomography while rotating around an object 1000 and acquires raw data corresponding thereto. Also, FIG. 10B is a diagram illustrating a reconstructed tomography image and a sinogram acquired by tomography.

The tomography apparatus 500 may irradiate an X-ray to an object, sense the X-ray that has passed through the object, and generate raw data corresponding to the X-ray.

Specifically, as discussed above, the tomography apparatus 500 may further include a gantry 102, and the gantry 102 may include an X-ray generator 106 and an X-ray detector 108. An X-ray generator 1002 in FIG. 10A may correspond to the X-ray generator 106 of FIG. 2. The X-ray generator 1002 of the tomography apparatus 500 irradiates an X-ray to the object 1000. When the tomography apparatus 500 performs tomography, the X-ray generator 1002 rotates around an object and acquires a plurality of raw data corresponding to the rotation angles. Specifically, since the X-ray detector 108 detects information about the X-rays transmitted from the X-ray generator 106 at various angles by rotating the gantry 102, the tomography apparatus 500 may perform tomography at various angles or views and generate raw data about the object. Accordingly, the tomography apparatus 500 acquires raw data 1012, 1014, and 1016 by sensing the X-rays applied to the object from positions P1, P2, and P3 respectively. Herein, the raw data 1012, 1014, and 1016 acquired respectively from the positions P1, P2, and P3 may be projection data acquired by irradiating the X-ray to the object 1000 from one view. Thus, in order to generate one cross-sectional tomography image, the tomography apparatus 500 should perform tomography while rotating the X-ray generator 1002 at least 180 degrees.

Referring to FIG. 10B, a sinogram 1020 may be acquired by combining a plurality of projection data acquired while moving the X-ray generator 1002 at each of predetermined angular intervals as illustrated in FIG. 10A. The sinogram 1020 may be acquired by performing tomography while rotating the X-ray generator 1002 one cycle, and the sinogram 1020 corresponding to the one-cycle rotation may be used to generate one cross-sectional tomography image. The one-cycle rotation may be about a half turn or more or about one turn or more according to the specification of a tomography system. Also, the sinogram 1020 may be filtered and then back-projected (filtered back-projection) to reconstruct a tomography image 1022.

However, as illustrated in FIG. 10A, when the gantry 102 is rotated in order for the X-ray generator 1002 of the tomography apparatus 500 to apply the X-rays from the respective positions such as P1, P2, and P3 and tomography is performed several times at various angles, the time taken to complete the tomography of the object may become relatively long. That is, as the tomography angle related to a tomography image of the object becomes diverse, the time taken for tomography may become relatively long. In order to solve this problem and acquire a high-quality tomography image in a short time, according to an exemplary embodiment, the tomography apparatus 500 may generate raw data corresponding to the result of tomography at a plurality of angles (as well as at a particular angle) by using information about the X-ray acquired through tomography at the particular angle.

Figure 11:
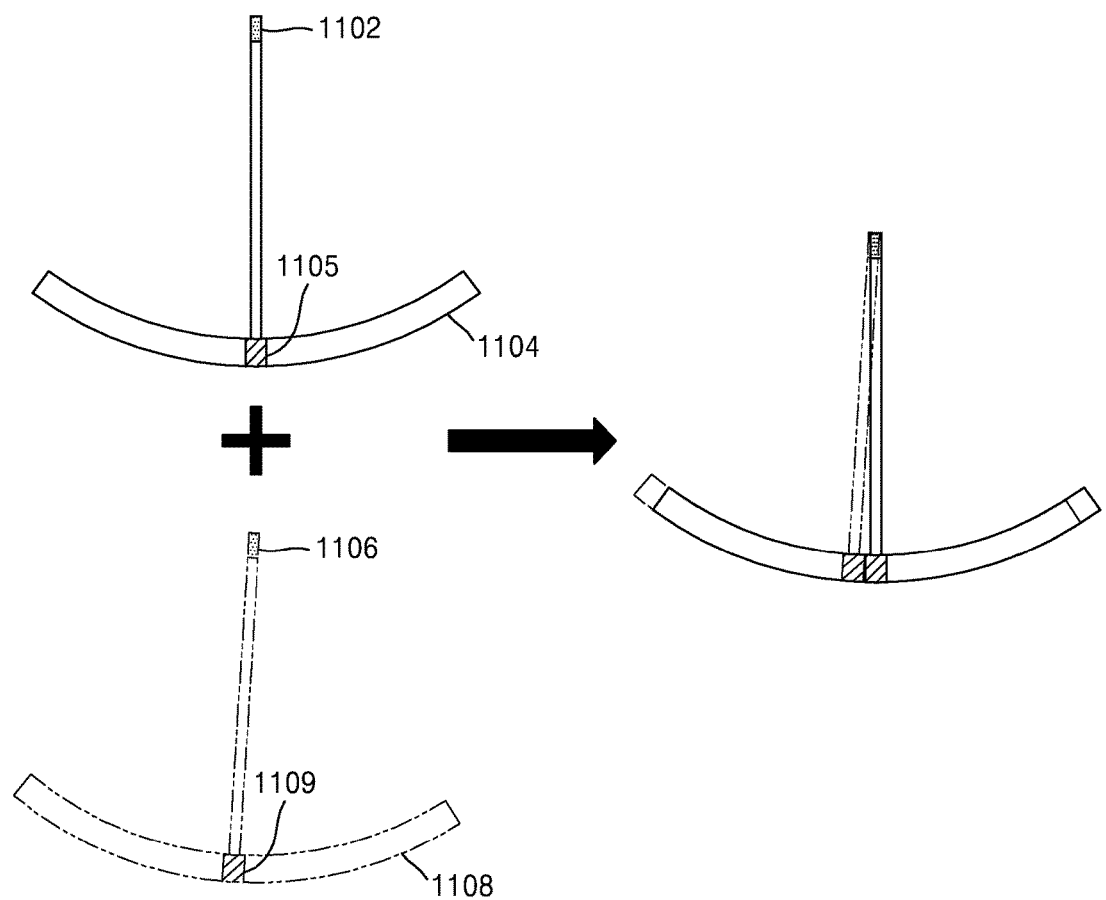
FIG. 11 illustrates another process of performing statistical learning-based ray splitting by a tomography apparatus by using information about an X-ray acquired by performing tomography at a particular angle according to an exemplary embodiment.

FIG. 11 illustrates another process of performing statistical learning-based ray splitting by the tomography apparatus 500 by using information about an X-ray acquired by performing tomography at a particular angle according to an exemplary embodiment.

According to an exemplary embodiment, in order to acquire a high-quality tomography image, the tomography apparatus 500 may perform statistical learning-based ray splitting as one of the tomography methods, and may generate raw data corresponding to the information acquired by performing tomography at other angles as well as at a particular angle, at which tomography is actually performed, by transmitting/receiving the X-rays. That is, according to an exemplary embodiment, as illustrated in FIG. 8, the tomography apparatus 500 may determine the third raw data corresponding to the raw data acquired by capturing a tomography image by using the virtual detector 704, by processing, through a statistical learning-based ray splitting process, the first raw data detected by the detector 702 by performing tomography at a particular angle. The third raw data corresponding to the raw data acquired through the virtual detector 704 may correspond to the raw data acquired by using more detector cells than the first raw data used in operation S800. The sinogram, for example, the sinogram acquired based on the third raw data may include more data in the arrangement of detector cells than the sinogram acquired based on the first raw data.

As described above, the tomography apparatus 500 may perform tomography on the object in various views while rotating the gantry 102, and thus may acquire raw data corresponding to the respective views. That is, as tomography is performed in various views, the sinogram 1020 based on the raw data may include more data in a y-axis direction 1040 perpendicular to an x-axis direction 1030 in which the detector cells are arranged. Accordingly, as the tomography apparatus 500 uses more detector cells, the x-axis direction resolution of the sinogram 1020 may increase; and as tomography is performed in more views, the y-axis direction resolution of the sinogram 1020 may increase. However, according to an exemplary embodiment, the tomography apparatus 500 may acquire raw data corresponding to the information acquired by tomography in another view, based on the result of tomography in a particular view. Accordingly, the time taken for performing tomography in various views may be reduced, and the y-axis direction resolution of the sinogram 1020 may be improved.

Referring to FIG. 11, when an X-ray generator 1102 included in the tomography apparatus 500 applies an X-ray, a detector cell 1105 on an X-ray detector 1104 may detect the X-ray that has passed through an object. According to an exemplary embodiment, the detector cell 1105 may be located on an axis of the X-ray applied by the X-ray generator 1102. The tomography apparatus 500 may perform a statistical learning-based ray splitting process based on the information about the X-ray detected by the detector cell 1105, and thus may increase the y-axis direction resolution of the sinogram 1020. That is, in the tomography apparatus 500, the detector cell 1105 of the X-ray detector 1104 may detect an X-ray applied in a first view by the X-ray generator 1102, and then a detector cell 1109 of an X-ray detector 1108 may detect an X-ray applied in a second view by an X-ray generator 1106. According to an exemplary embodiment, the tomography apparatus 500 may generate a sinogram of the object by using the information about the detected X-ray and may perform statistical learning-based ray splitting by using the information about the detected X-ray. The tomography apparatus 500 may process the information about the X-rays (for example, the amount of photons), which are detected in the first view and the second view, through statistical learning-based ray splitting and use the processed information to generate a high-resolution tomography image.

Figure 12:
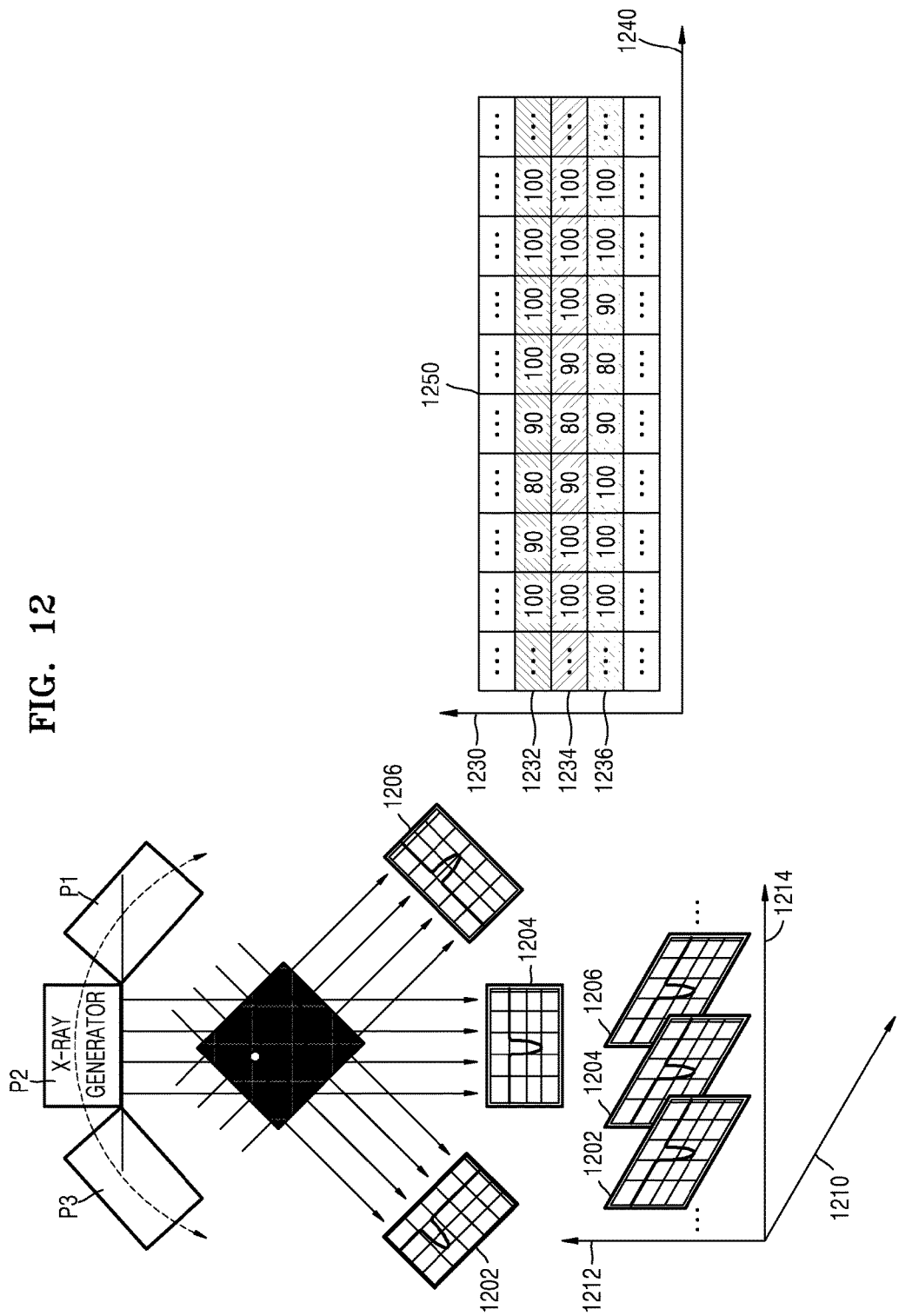
FIG. 12 illustrates a process of acquiring raw data about a sinogram having an improved resolution in a view direction by a tomography apparatus through statistical learning-based ray splitting according to an exemplary embodiment.

FIG. 12 illustrates a process of acquiring raw data about a sinogram having an improved resolution in a view direction by the tomography apparatus 500 through statistical learning-based ray splitting according to an exemplary embodiment.

According to an exemplary embodiment, the tomography apparatus 500 may acquire raw data 1202 about a first view, raw data 1204 about a second view, and raw data 1206 about a third view. The acquired raw data 1202, 1204, and 1206 may include information about X-rays acquired in different views, and when a one-dimensional data matrix is converted into a sinogram, it may be arranged in the view direction of the sinogram to be represented as a 2D sinogram. That is, the respective raw data 1202, 1204, and 1206 acquired in the respective views may be represented in a second axis 1212 representing the value of raw data corresponding to a first axis 1210 corresponding to the arrangement direction of detector cells, and the raw data 1202, 1204, and 1206 acquired in the respective views may be arranged with respect to a third axis 1214 related to the view direction. When the values of information about the X-rays detected by the respective detector cells are arranged in the first axis 1210 corresponding to the arrangement direction of detector cells and the third axis 1214 related to the view direction, it may be represented as a sinogram, and the sinogram may be schematized as a data matrix 1250 representing the values represented by the information about the X-rays. The data matrix 1250 corresponding to the sinogram may include data arranged in a detector cell arrangement direction 1240 and a view direction 1230, wherein the detector cell arrangement direction 1240 may be a direction corresponding to the first axis 1210 and the view direction 1230 may be a direction corresponding to the third axis 1214. Thus, data rows 1232, 1234, and 1236 arranged in the view direction 1230 may correspond to the information about the X-rays represented by the raw data 1202, 1204, and 1206 acquired in the respective views (for example, the amount of photons detected by the respective detector cells).

Figure 13A:
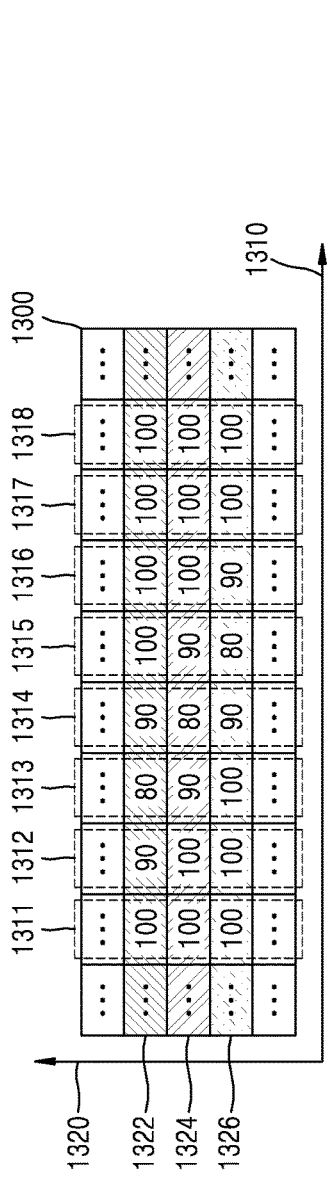
FIGS. 13A, 13B, and 13C illustrate a process of performing statistical learning-based ray splitting by a tomography apparatus by using a data matrix including values represented by information about X-rays according to an exemplary embodiment.
Figure 13B:
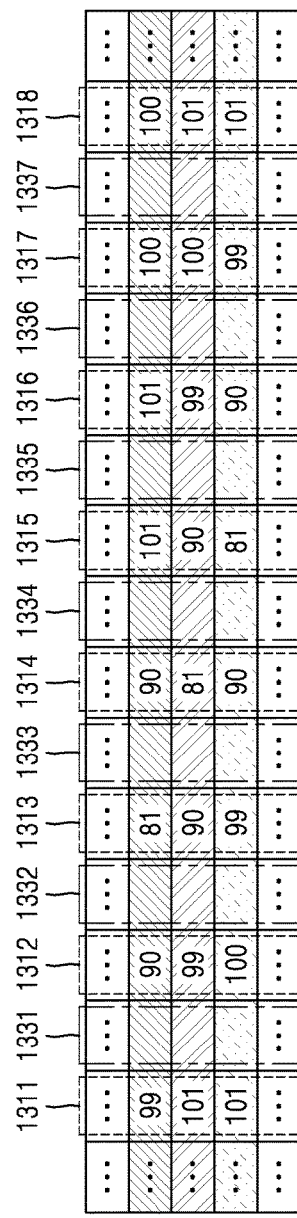
Figure 13C:
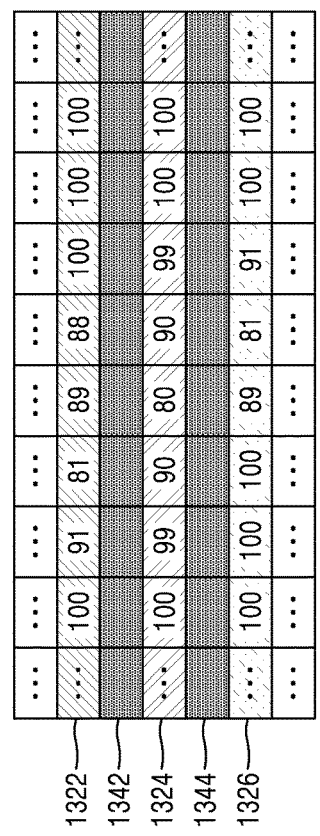

FIGS. 13A, 13B, and 13C illustrate a process of performing statistical learning-based ray splitting by the tomography apparatus 500 by using a data matrix 1300 including values represented by information about X-rays according to an exemplary embodiment.

Referring to FIG. 13A, the data matrix 1300 including the values represented by the information about the X-rays may be acquired based on the information about the X-rays acquired by the tomography apparatus 500, and the tomography apparatus 500 may represent a sinogram based on the acquired data matrix. Specifically, the data matrix 1300 may be acquired with respect to a detector cell arrangement direction 1310 and a view direction 1320 corresponding to an imaging angle that may vary according to the rotation of the gantry 102. That is, among the data constituting the data matrix 1300, data 1322, 1224, and 1326 located in the same column may correspond to data about the X-rays acquired by tomography in the same view; and data 1311, 1312, 1313, 1314, 1315, 1316, 1317, and 1318 located in the same row may correspond to data about the X-rays acquired by the same detector cell. The data included in the data matrix 1300 may be processed by statistical learning-based ray splitting as a tomography method that may be performed according to an exemplary embodiment, and the processed data may be used to generate a high-resolution tomography image.

According to an exemplary embodiment, the tomography apparatus 500 may perform statistical learning-based ray splitting with respect to the detector cell arrangement direction 1310 by using the data matrix 1300. Referring to FIG. 13B, data 1311, 1312, 1313, 1314, 1315, 1316, 1317, and 1318 about the X-rays detected by the respective detector cells included in the detector 702 may be processed according to the performance of statistical learning-based ray splitting according to an exemplary embodiment, and the processed data may be used to determine information about the X-rays acquired by the detector cells included in the virtual detector 704 in each view. In FIG. 13B, the data 1311, 1312, 1313, 1314, 1315, 1316, 1317, and 1318 about the X-rays in each view may correspond to the first raw data or the second raw data in the above exemplary embodiments. That is, when the data 1311, 1312, 1313, 1314, 1315, 1316, 1317, and 1318 about the X-rays corresponds to the first raw data, it may be processed into the second raw data through the second raw data determining process of operation S502; and when the data 1311, 1312, 1313, 1314, 1315, 1316, 1317, and 1318 about the X-rays in the view corresponds to the second raw data, it may be directly used in operation S504 for determining the third raw data.

Referring to FIG. 13B, when ray splitting is performed, data 1331, 1332, 1333, 1334, 1335, 1336, and 1337 about the X-rays acquired by the detector cells included in the virtual detector 704 may be further included between the data 1311, 1312, 1313, 1314, 1315, 1316, 1317, and 1318 about the X-rays acquired by the detector cells. In order to generate a high-resolution tomography image, the tomography apparatus may use the third raw data including the data 1311, 1312, 1313, 1314, 1315, 1316, 1317, and 1318 about the X-rays corresponding to the second raw data and the data 1331, 1332, 1333, 1334, 1335, 1336, and 1337 generated through the ray splitting process. However, since specific data values illustrated in FIG. 13B are merely examples for describing various exemplary embodiments, the exemplary embodiments are not limited to the specific data values. Also, the values represented by the data 1311, 1312, 1313, 1314, 1315, 1316, 1317, and 1318 about the X-rays corresponding to the second raw data after being processed through the ray splitting process may represent the same values as those before performing the ray splitting, but they may be changed into different values according to the processing results. Since the statistical learning-based ray splitting performed with respect to the detector cell arrangement direction 1310 has been described above with reference to various exemplary embodiments corresponding to FIGS. 5 to 9, detailed descriptions thereof will be omitted herein for conciseness. According to the ray splitting in FIG. 13B, the tomography apparatus 500 may generate the third tomography image corresponding to the tomography image acquired by using the information about the X-rays acquired by using the virtual detector 704 including more detector cells than the first tomography image. That is, by performing the ray splitting with respect to the detector cell arrangement direction, even without physically using the more detector cells, the tomography apparatus 500 may generate the third tomography image having a higher resolution than the second tomography image acquired through a simple upscaling process (e.g., interpolation). Accordingly, when the ray splitting of FIG. 13B is performed, a sinogram having a relatively higher resolution in the detector cell arrangement direction may be represented and the tomography apparatus 500 may generate the third tomography image by using the high-resolution sinogram.

According to an exemplary embodiment, the tomography apparatus 500 may perform statistical learning-based ray splitting with respect to the view direction 1320 by using the data matrix 1300.

Referring to FIG. 3C, data 1322, 1324, and 1326 about the X-rays detected in each view may be processed according to the performance of statistical learning-based ray splitting according to an exemplary embodiment, and the processed data may be used to determine information about the X-rays acquired by performing virtual image capturing in other views than various views in which tomography images are captured. In FIG. 13C, the data 1322, 1324, and 1326 about the X-rays in each view may correspond to the first raw data or the second raw data in the above exemplary embodiments. That is, when the data 1322, 1324, and 1326 about the X-rays corresponds to the first raw data, it may be processed into the second raw data through the second raw data determining process of operation S502; and when the data 1322, 1324, and 1326 about the X-rays in the view corresponds to the second raw data, it may be directly used in operation S504 for determining the third raw data.

Referring to FIG. 13C, when ray splitting is performed, data 1342 and 1344 about the X-rays acquired in other views may be further included between the data 1322, 1324, and 1326 about the X-rays acquired in each view. In order to generate a high-resolution tomography image, the tomography apparatus may use the third raw data including the data 1322, 1324, and 1326 about the X-rays corresponding to the second raw data and the data 1331, 1342, and 1344 generated through the ray splitting process. However, since specific data values illustrated in FIG. 13C are merely examples for describing various exemplary embodiments, the exemplary embodiments are not limited to the specific data values. Also, the values represented by the data 1322, 1324, and 1326 about the X-rays corresponding to the second raw data after being processed through the ray splitting process may represent the same values as those before performing the ray splitting, but they may be changed into different values according to the processing results. Since the statistical learning-based ray splitting performed with respect to the view direction 1320 has been described above with reference to various exemplary embodiments corresponding to FIGS. 10 to 12, detailed descriptions thereof will be omitted herein for conciseness. According to the ray splitting in FIG. 13C, the tomography apparatus 500 may generate a tomography image including more data in the view direction than the first tomography image. That is, by performing tomography at various angles, even without consuming time, the third tomography image corresponding to the result of performing tomography at relatively more angles than the first tomography image may be generated through the ray splitting. Accordingly, when the ray splitting of FIG. 13C is performed, a sinogram having a relatively higher resolution in the view direction may be represented and the tomography apparatus 500 may generate the third tomography image by using the high-resolution sinogram.

According to an exemplary embodiment, the tomography apparatus 500 may perform statistical learning-based ray splitting with respect to the detector cell arrangement direction 1310 and the view direction 1320 by using the data matrix 1300. That is, the statistical learning-based ray splitting processes performed with respect to different directions, which have described above with reference to FIGS. 13B and 13C, may all be performed. By performing the ray splitting with respect to the view direction 1320 while performing the ray splitting with respect to the detector cell arrangement direction 1310, the tomography apparatus 500 may acquire a high-resolution sinogram in the detector cell arrangement direction and the view direction, which is a tomography image corresponding to the capturing of tomography images in relatively more views by using relatively more detector cells. The tomography apparatus 500 may generate the third tomography image by using the high-resolution sinogram in the detector cell arrangement direction and the view direction. The tomography apparatus 500 may perform the statistical learning-based ray splitting in the detector cell arrangement direction and the view direction, regardless of their order. Thus, the ray splitting in the detector cell arrangement direction may be first performed, the ray splitting in the view direction may be first performed, or the ray splitting in the detector cell arrangement direction and the ray splitting in the view direction may be simultaneously performed.

As described above, according to one or more of the above exemplary embodiments, the raw data about the high-resolution tomography image may be recursively generated through the statistical learning-based raw data generating method, and the generated high-resolution tomography image may have a relatively increased resolution in at least one of the detector cell arrangement direction and the view direction for tomography.

Exemplary embodiments may be written as computer programs and may be implemented in general-purpose digital computers that execute the programs by using a computer-readable recording medium.

Examples of the computer-readable recording medium include magnetic storage media (e.g., ROM, floppy disks, hard disks, etc.), optical recording media (e.g., CD-ROMs, DVDs, etc.), and transmission media such as Internet transmission media.

While one or more exemplary embodiments have been described with reference to the accompanying drawings, those of ordinary skill in the art will readily understand that various modifications are possible in the exemplary embodiments without materially departing from the concepts and features of the exemplary embodiments. Therefore, it is to be understood that the exemplary embodiments described above should be considered in a descriptive sense only and not for purposes of limitation.

It should be understood that exemplary embodiments described herein should be considered in a descriptive sense only and not for purposes of limitation. Descriptions of features or aspects within each embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A tomography method for generating a computed tomography (CT) image, the tomography method comprising:
   generating a first tomography image based on first raw data corresponding to a received X-ray comprising acquired photons;
   determining second raw data by generating a second tomography image having an increased resolution in comparison with the first tomography image and performing forward projection on the second tomography image;
   determining third raw data based on a first parameter, the first raw data, and the second raw data; and
   generating a third tomography image based on the third raw data,
   wherein the determining of the third raw data is based on information about a distribution of the acquired photons and a number of the acquired photons, the information being included in at least one from among the first raw data and the second raw data,
   wherein the second tomography image has the increased resolution in comparison with the first tomography image in an arrangement direction of a detector cell detecting the X-ray.

2. The tomography method of claim 1, wherein
   the third raw data has a same data amount as the first raw data; and
   the data amount is based on the number of the acquired photons.

3. The tomography method of claim 1, wherein the determining of the third raw data comprises determining a third matrix including the third raw data using a first matrix including the first raw data and a second matrix representing the first parameter, and
   the determining of the third raw data is based on a difference between the third raw data and the second raw data.

4. The tomography method of claim 1, wherein:
   the determining of the third raw data comprises determining a third matrix including the third raw data by using a first matrix including the first raw data and a second matrix representing the first parameter;
   the determining of the third raw data is based on a difference between the third raw data and the second raw data;
   the third raw data has a same data amount as the first raw data; and
   the first matrix and the third matrix have different sizes.

5. The tomography method of claim 1, further comprising:
   acquiring a fourth tomography image by performing backward projection on the third raw data; and
   determining refined second raw data by performing forward projection on the fourth tomography image.

6. The tomography method of claim 1, wherein the determining of the third raw data comprises:
   determining a second parameter representing an expected value of the third raw data; and
   determining the third raw data by using the first raw data and the second parameter.

7. The tomography method of claim 6, further comprising:
   generating a changed second parameter; and
   determining a new third raw data using the changed second parameter,
   wherein the changed second parameter maximizes a similarity between the new third raw data and the first raw data.

8. The tomography method of claim 1, wherein
   the received X-ray is acquired by performing tomography on an object using a plurality of views;
   the second tomography image has the increased resolution in comparison with the first tomography image in a view direction of at least one view from among the plurality of views.

9. The tomography method of claim 8, wherein
the second tomography image has the increased resolution in comparison with the first tomography image in the view direction and an arrangement direction of a detector cell detecting the X-ray.

10. A tomography apparatus for generating a tomography image, the tomography apparatus comprising:
a receiver configured to receive first raw data corresponding to a received X-ray comprising acquired photons; and
a processor configured to generate a first tomography image based on the first raw data, determine second raw data by generating a second tomography image having an increased resolution in comparison with the first tomography image and performing forward projection on the second tomography image, determine third raw data based on a first parameter, the first raw data, and the second raw data, and generate a third tomography image based on the third raw data,
wherein the processor is further configured to determine the third raw data based on information about a distribution of the acquired photons and a number of the acquired photons, the information being included in at least one from among the first raw data and the second raw data,
wherein the second tomography image has the increased resolution in comparison with the first tomography image in a direction of arrangement of a detector cell detecting the X-ray.

11. The tomography apparatus of claim 10, wherein
the third raw data has a same data amount as the first raw data; and
the data amount is based on the number of the acquired photons.

12. The tomography apparatus of claim 10, wherein
the processor is further configured to determine a third matrix including the third raw data using a first matrix including the first raw data and a second matrix representing the first parameter;
the processor is further configured to determine the third raw data based on a difference between the third raw data and the second raw data; and
the first matrix and the third matrix have different sizes.

13. The tomography apparatus of claim 10, wherein
the processor is further configured to determine a third matrix including the third raw data using a first matrix including the first raw data and a second matrix representing the first parameter;
the processor is further configured to determine the third raw data based on a difference between the third raw data and the second raw data;
the third raw data has a same data amount as the first raw data; and
the first matrix and the third matrix have different sizes.

14. The tomography apparatus of claim 10, wherein the processor is further configured to acquire a fourth tomography image by performing backward projection on the third raw data and determines refined second raw data by performing forward projection on the fourth tomography image.

15. The tomography apparatus of claim 10, wherein the processor is further configured to determine a second parameter representing an expected value of the third raw data, and to determine the third raw data by using the first raw data and the second parameter.

16. The tomography apparatus of claim 15, wherein the processor is further configured to:
generate a changed second parameter ; and
determine a new third raw data by using the changed second parameter;
wherein the changed second parameter maximizes a similarity between the new third raw data and the first raw data.

17. The tomography apparatus of claim 10, wherein
the received X-ray is acquired by performing tomography on an object using a plurality of views;
the second tomography image has the increased resolution in comparison with the first tomography image in a view direction of at least one view from among the plurality of views.

18. A non-transitory computer-readable recording medium configured to store instructions thereon, the instructions including a program which, when executed by a processor, cause the processor to perform the tomography method of claim 1.

* * * * *